US010877046B2

(12) United States Patent
Brohman et al.

(10) Patent No.: US 10,877,046 B2
(45) Date of Patent: Dec. 29, 2020

(54) TREATMENT OF SPONTANEOUS PRETERM BIRTH

(71) Applicant: NX Prenatal Inc., Louisville, KY (US)

(72) Inventors: Brian D. Brohman, Louisville, KY (US); Zhen Zhang, Dayton, MD (US); Kevin S. Goudy, Decatur, GA (US); Robert C. Doss, Lexington, KY (US); Alan M. Ezrin, Miami, FL (US); Kevin Paul Rosenblatt, Bellaire, TX (US)

(73) Assignee: NX PRENATAL INC., Louisville, KY (US)

( * ) Notice: Subject to any disclaimer, the term of this patent is extended or adjusted under 35 U.S.C. 154(b) by 82 days.

(21) Appl. No.: 15/997,540

(22) Filed: Jun. 4, 2018

(65) Prior Publication Data

US 2019/0041391 A1   Feb. 7, 2019

Related U.S. Application Data

(63) Continuation of application No. PCT/US2016/065024, filed on Dec. 5, 2016.

(60) Provisional application No. 62/263,549, filed on Dec. 4, 2015.

(51) Int. Cl.
*G01N 33/68* (2006.01)
*B01D 61/14* (2006.01)
*G01N 30/02* (2006.01)

(52) U.S. Cl.
CPC ......... *G01N 33/689* (2013.01); *B01D 61/145* (2013.01); *G01N 30/02* (2013.01); *G01N 33/6848* (2013.01); *G01N 2030/027* (2013.01); *G01N 2800/368* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 9,068,990 | B2 | 6/2015 | Taylor et al. |
| 9,417,249 | B2 | 8/2016 | Taylor et al. |
| 10,247,736 | B2 | 4/2019 | Graves et al. |
| 2010/0137263 | A1 | 6/2010 | Smith |
| 2010/0190652 | A1 | 7/2010 | Nagalla et al. |
| 2010/0297679 | A1 | 11/2010 | Graves et al. |
| 2011/0236953 | A1 | 9/2011 | Walsh et al. |
| 2012/0021442 | A1 | 1/2012 | Buhimschi et al. |
| 2013/0058931 | A1 | 3/2013 | Taylor et al. |
| 2014/0186332 | A1 | 7/2014 | Ezrin et al. |
| 2014/0287950 | A1 | 9/2014 | Hickok et al. |
| 2015/0355188 | A1 | 12/2015 | Ezrin et al. |
| 2016/0375025 | A1 | 12/2016 | Boshoff et al. |
| 2017/0022565 | A1 | 1/2017 | Boniface et al. |

FOREIGN PATENT DOCUMENTS

| | | |
|---|---|---|
| WO | WO-2008/056114 A1 | 5/2008 |
| WO | WO-2008/063928 A2 | 5/2008 |
| WO | WO-2008/063928 A3 | 8/2008 |
| WO | WO-2008/098734 A1 | 8/2008 |
| WO | WO-2009/031721 A1 | 3/2009 |
| WO | WO-2011/112993 A2 | 9/2011 |
| WO | WO-2011/112993 A3 | 9/2011 |
| WO | WO-2012/174282 A2 | 12/2012 |
| WO | WO-2012/174282 A3 | 12/2012 |
| WO | WO-2013/040211 A1 | 3/2013 |
| WO | WO-2013/184830 A1 | 12/2013 |
| WO | WO-2014/105985 A1 | 7/2014 |
| WO | WO-2014/110098 A1 | 7/2014 |
| WO | WO-2014/144129 A2 | 9/2014 |
| WO | WO-2014/144129 A3 | 9/2014 |
| WO | WO-2014/160237 A2 | 10/2014 |
| WO | WO-2014/160237 A3 | 10/2014 |
| WO | WO-2017/096405 A1 | 6/2017 |
| WO | WO-2019/152745 A1 | 8/2019 |

OTHER PUBLICATIONS

UWPR University of Washington Proteomics Resource, Protein Reduction, Alkylation, Digestion, Oct. 4, 2011, pp. 1-8. (Year: 2011).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Van Der Vekiens et al., Human and equine cardiovascular endocrinology: beware to compare, Cardiovascular Endocrinology 2013, vol. 2, No. 4, pp. 67-76. (Year: 2013).*
Ables, A.Z. et al. (2005). "Preterm Labor: Diagnostic and Therapeutic Options are Not All Alike," *The Journal of Family Practice* 54(3):245-252.
Atay, S. et al. (2011). "Trophoblast-Derived Exosomes Mediate Monocyte Recruitment and Differentiation," *American Journal of Reproductive Immunology* 65:65-77.
Beer, L.A. et al. (2011). "Systematic Discovery of Ectopic Pregnancy Serum Biomarkers Using 3-D Protein Profiling Coupled with Label-free Quantitation," *Journal of Proteome Research* 10(3)1126-1138.
Behrman, R.E. et al. (2007). "Diagnosis and treatment of conditions leading to spontaneous preterm birth," National Institute of Health, 27 pages.
Berghella, V. et al. (2011). "Cerclage for short cervix on ultrasonography in women with singleton gestations and previous preterm birth: a meta-analysis," *Obst. Gyn.* 117(3):663-671.
Buhimschi, I.A. et al. (2005). "Proteomic Biomarker Analysis of Amniotic Fluid for Identification of Intra-Amniotic Inflammation," *BJOG: An International Journal of Obstetrics and Gynaecology* 112:173-181.

(Continued)

Primary Examiner — Gary Counts
(74) Attorney, Agent, or Firm — Cooley LLP

(57) ABSTRACT

Provided herein are proteomic biomarkers of spontaneous preterm birth, proteomic biomarkers of term birth, and methods of use thereof. In particular, provided are tools for determining whether a pregnant subject is at an increased risk for premature delivery, as well as tools for decreasing a pregnant subject's risk for premature delivery.

13 Claims, 12 Drawing Sheets

(56) References Cited

OTHER PUBLICATIONS

Buhimschi, C.S. et al. (2007). "Proteomic Biomarkers of Adverse Pregnancy Outcome in Preterm Birth: A Theranostics Opportunity," B;bertliev. Obstet. Gynecol. 2(6):743-753.
Conde-Agudelo, A. et al. (2011). "Novel Biomarkers for the Prediction of the Spontaneous Preterm Birth Phenotype: A Systematic Review and Meta-Analysis," BJOG: An International Journal of Obstetrics and Gynaecology, pp. 1042-1054.
Da Fonseca, E.B. et al. (2003). "Prophylactic administration of progesterone by vaginal suppository to reduce the incidence of spontaneous preterm birth in women at increased risk: A randomized placebo-controlled double-blind study," Am. J. Obstetrics Gynecology 188(2):419-424.
De Menezes-Neto, A. et al. (2015). "Size-exclusion chromatography as a stand-alone methodology identifies novel markers in mass spectrometry analyses of plasma-derived vesicles from healthy individuals," J. Extracellular Vesicles 4:27378, 14 pages.
Extended European Search Report dated Aug. 29, 2016, for European Patent Application No. 13 867 314.0, filed on Dec. 26, 2013, 18 pages.
Esplin, M.S. et al. (2011). "Proteomic Identification of Serum Peptides Predicting Subsequent Spontaneous Preterm Birth," American Journal of Obstetrics & Gynecology 204:391.e1-391.e8.
Ezrin, A.M. et al. (2015). "Circulating serum-derived microparticles provide novel proteomic biomarkers of spontaneous preterm birth," Am. J. Perinatol. 32:605-614.
Final Office Action dated Mar. 3, 2016, for U.S. Appl. No. 13/797,933, filed Mar. 12, 2013, 11 pages.
Final Office Action dated Nov. 16, 2018, for U.S. Appl. No. 13/797,933, filed Mar. 12, 2013, 22 pages.
Final Office Action dated Apr. 19, 2017, for U.S. Appl. No. 14/655,705, filed Jun. 25, 2015, 13 pages.
Final Office Action dated Nov. 16, 2018, for U.S. Appl. No. 14/655,705, filed Jun. 25, 2015, 22 pages.
Gercel-Taylor, C. et al. (2012). "Nanoparticle Analysis of Circulating Cell-Derived Vesicles in Ovarian Cancer Patients," Analytical Biochemistry 428:44-53.
Goldenberg, R.L. et al. (2005). "Biochemical Markers for the Prediction of Preterm Birth," American Journal of Obstetrics & Gynecology 192:S36-S46.
Goldenberg, R.L. et al. (2008). "Preterm Birth 1: Epidemiology and Causes of Preterm Birth," The Lancet 371:75-84.
Gupta, S. et al. (2012). "17-α hydroxyprogesterone caproate for the prevention of preterm birth," Women's Health London 8(1):21-30.
Hassan, S.S. et al. (2011). "Vaginal progesterone reduces the rate of preterm birth in women with a sonographic short cervix: a multicenter, randomized, double-blind, placebo-controlled trial," Ultrasound in Obstetrics and Gynecology 38(1):18-31.
Honest et al., "Screening to Prevent Spontaneous Preterm Birth: Systematic Reviews of Accuracy and Effectiveness Literature with Economic Modelling", Health Technology Assessment, vol. 13, No. 43, Chapter. 1, Sep. 2009, pp. 17 pages.
Intermountain Healthcare (2014). Cervical Cerclage, 2 pages.
Intermountain Healthcare (2014). Prevention and Management of Preterm Birth, 28 pages.
Intermountain Healthcare (2014). 17P for preventing preterm birth, 2 pages.
International Search Report dated Mar. 21, 2014, for PCT Application No. PCT/US2013/077868, filed on Dec. 26, 2013, 3 pages.
International Search Report dated Feb. 21, 2017, for PCT Application No. PCT/US2016/065024, filed on Dec. 5, 2016, 3 pages.
International Preliminary Report on Patentability dated Jun. 30, 2015, for PCT Application No. PCT/US2013/077868, filed on Dec. 26, 2013, 9 pages.
Koenig, T. et al. (2008). "Robust Prediction of the Mascot Score for an Improved Quality Assessment in Mass Spectrometric Proteomics," Journal of Proteome Research 7(9):3708-3717.

Liu, C. et al. (2011). "Proteomic analysis of human serum for Finding pathogenic factors and potential biomarkers in preeclampsia," Placenta 32:168-174.
Mathivanan, S. et al. (2011). "ExoCarta 2012: Database of Exosomal Proteins, RNA and Lipids," Nucleic Acids Research 40:D1241-D1244.
Mincheva-Nilsson, L. (2010). "Placental Exosome-Mediated Immune Protection of the Fetus: Feeling Groovy in a Cloud of Exosomes," Expert Review of Obstetrics & Gynecology 5(5):619-634.
National Research Council (2007). "Diagnosis and Treatment of Conditions Leading to Spontaneous Preterm Birth," The National Academies Press, pp. 259-307.
Non-Final Office Action dated Mar. 13, 2015, for U.S. Appl. No. 13/797,933, filed Mar. 12, 2013, 14 pages.
Non-Final Office Action dated Jul. 14, 2016, for U.S. Appl. No. 14/655,705, filed Jun. 25, 2015, 11 pages.
Non-Final Office Action dated Jun. 7, 2017, for U.S. Appl. No. 13/797,933, filed Mar. 12, 2013, 19 pages.
Non-Final Office Action dated Dec. 8, 2017, for U.S. Appl. No. 14/655,705, filed Jun. 25, 2015, 18 pages.
Olver, C. et al. (2007). "Proteomic Analysis of Secreted Exosomes," Subcellular Biochemistry 43:99-131.
Pant, S. et al. (2012). "The Multifaceted Exosome: Biogenesis, Role in Normal and Aberrant Cellular Function, and Frontiers for Pharmacological and Biomarker Opportunities," Biochemical Pharmacology 83:1484-1494.
Pappin, D.J.C. et al. (1993). "Rapid Identification of Proteins by Peptide-Mass Fingerprinting," Current Biology 3(6):327-332.
Partial European Search Report dated May 3, 2016, for European Patent Application No. 13 867 314.0, filed on Dec. 26, 2013, 11 pages.
Pereira et al. (2010). "Insights into the multifactorial nature of preterm birth: proteomic profiling of the maternal serum glycoproteome and maternal serum peptidome among women in preterm labor," American Journal of Obstetrics and Gynecology 202:555-558.
Pereira, L. et al. (2007). "Identification of novel protein biomarkers of preterm birth in human cervical-vaginal fluid," J. Proteome Res. 6:1269-1276.
Perkins, D.N. et al. (1999). "Probability-Based Protein Identification by Searching Sequence Databases Using Mass Spectrometry Data," Electrophoresis 20:3551-3567.
Practice Bulletin No. 130 (2012). "Prediction and Prevention of Preterm Birth," Obstetrics & Gynecology 120(4):964-973.
Redman, C.W.G. et al. (2012). "Review: Does Size Matter? Placental Debris and the Pathophysiology of Pre-Eclampsia," Trophoblast Research 33(Supplement A) 26:S48-S54.
Sabapatha, A. et al. (2006). "Specific Isolation of Placenta-Derived Exosomes from the Circulation of Pregnant Women and Their Immunoregulatory Consequences," American Journal of Reproductive Immunology 56:345-355.
Saunders, R.D. et al. (2012). "Alterations in Antibody Subclass Immune Reactivity to Trophoblast-derived Fetal Fibronectin and a2-Macroglobulin in Women with Recurrent Pregnancy Loss," American Journal of Reproductive Immunology 68:438-449.
Shah, S.J. et al. (2009). "Identification and Quantification of Preterm Birth Biomarkers in Human Cervicovaginal Fluid by Liquid Chromatography/Tandem Mass Spectrometry," Journal of Proteome Research 8(5):2407-2417.
Simpson, R.J. et al. (2008). "Proteomic Profiling of Exosomes: Current Perspectives," Proteomics 8:4083-4099.
Singh, P.P. et al. (2012). "Exosomes Isolated from Mycobacteria-Infected Mice or Cultured Macrophages can Recruit and Activate Immune Cells in Vitro and in Vivo," Journal of Immunology 189(2):777-785.
Society for Maternal-Fetal Medicine and the SMFM Foundation (2015). "High-risk pregnancy care, research, and education for over 35 years," 34 pages.
Stella, C.L. et al. (2009). "Preterm Labor Biomarker Discovery in Serum Using 3 Proteomic Profiling Methodologies," American Journal of Obstetrics & Gynecology 387:.e1-387.e13.
Stenczer, B. et al. (2012). "Circulating levels of thrombospondin-1 are decreased in HELLP syndrome," Thrombosis Research 129:470-473.

(56) References Cited

OTHER PUBLICATIONS

Tang, H-Y. et al. (2011). "Rapid Verification of Candidate Serological Biomarkers Using Gel-based, Label-free Multiple Reaction Monitoring," *Journal Proteome Research* 10:4005-4017.

Taylor, D.D. et al. (2006). "Pregnancy-Associated Exosomes and their Modulation of T cell Signaling," *The Journal of Immunology* 176:1534-1542.

Taylor, DD. Et al. (2011). "Exosome isolation for proteomic analyses and RNA profiling," *Methods Mol. Biol.* 728:235-246.

Thery, C. (2011). "Exosomes: Secreted Vesicles and Intercellular Communications," *F1000 Biology Reports* 3(15):1-8.

Tita, A.T.N. et al. (2009). "Progesterone for Preterm Birth Prevention: An Evolving Intervention," *American Journal of Obstetrics & Synecology* 200(3):219-224.

Wen, Q. et al. (2013). "Peptidomic Identification of Serum Peptides Diagnosing Preeclampsia," *PLoS One* 8(6):e65571.

Weismiller, D.G. (1999). "Preterm labor," *Am. Fam. Physician* 59(3):593-602.

Written Opinion of the International Searching Authority dated Mar. 21, 2014, for PCT Application No. PCT/US2013/077868, filed on Dec. 26, 2013, 8 pages.

Written Opinion of the International Searching Authority dated Feb. 21, 2017, for PCT Application No. PCT/US2016/065024, filed on Dec. 5, 2016, 10 pages.

International Preliminary Report on Patentability dated Jun. 5, 2018, for PCT Application No. PCT/US2016/065024, filed on Dec. 5, 2016, 11 pages.

Cantonwine, D. E. et al. "Evaluation of proteomic biomarkers associated with circulating microparticles as an effective means to stratify the risk of spontaneous preterm birth", Am J Obstet Gynecol. ;214(5):631. May 2016. Epub Feb. 11, 2016.

Extended European Search Report dated Aug. 22, 2019, for European Patent Application No. 16871740.3, filed on Dec. 26, 2013, 5 pages.

International Search Report and Written Opinion dated Apr. 24, 2019 for International Patent Application No. PCT/US2019/016192, filed Jan. 31, 2019, 11 pages.

McElrath, T., et al., "Extracellular vesicle proteomic markers obtained at 12 weeks predict spontaneous preterm birth less than 35 weeks gestation: a validation with specific characterization of marker behavior by fetal gender and parity", American Journal of Obstetrics and Gynecology; 128(1);14:S12. Jan. 2018.

International Preliminary Report on Patentability dated Aug. 4, 2020, for PCT Application No. PCT/US2019/016192, filed Jan. 31, 2019, 8 pages.

Non-Final Office Action dated Jun. 25, 2020, for U.S. Appl. No. 14/655,705, filed Jun. 25, 2015, 6 pages.

Notice of Allowance dated Oct. 6, 2020, for U.S. Appl. No. 14/655,705, filed on Jun. 25, 2015, 9 pages.

\* cited by examiner

TREATMENT OF SPONTANEOUS PRETERM BIRTH

CROSS-REFERENCE TO RELATED APPLICATIONS

This application is a continuation of International Application No. PCT/US2016/065024, filed on Dec. 5, 2016, which claims the benefit of priority to U.S. Provisional Application No. 62/263,549, filed on Dec. 4, 2015 which are hereby incorporated by reference in their entirety for all purposes.

BACKGROUND OF THE INVENTION

Preterm birth is a leading cause of neonatal morbidity and death in children less than 5 years of age, with deliveries at the earlier gestational ages exhibiting a dramatically increased risk (Liu et al., Lancer, 385:61698-61706, 2015; and Katz et al., Lancet, 382:417-425, 2013). Compared with infants born after 38 weeks, the composite rate of neonatal morbidity doubles for each earlier gestational week of delivery according to the March of Dimes. Approximately two thirds of spontaneous preterm births are spontaneous in nature, meaning they are not associated with medical intervention (Goldenberg et al., Lancet, 371:75-84, 2008; and McElrath et al., Am J Epidemiol, 168:980-989, 2008). Yet, despite the compelling nature of this condition, there has been little recent advancement in our understanding of the etiology of spontaneous preterm birth (SPTB). While there is an increasing consensus that SPTB represents a syndrome rather than a single pathologic entity, it has been both ethically and physically difficult to study the pathophysiology of the utero-placental interface (Romero et al., Science, 345:760-765, 2014). The evolving field of circulating microparticle (CMP) biology may offer a solution to these difficulties as these particles present a sampling of the utero-placental environment. Additionally, studying the contents of these particles holds the promise of identifying novel blood-based, and clinically useful, biomarkers.

Microparticles are membrane-bound vesicles that range in size from 50-300 nm and shed by a wide variety of cell types. Microparticle nomenclature varies, but typically microparticles between 50-100 nm are called exosomes, those >100 nm are termed microvesicles and other terms, such as microaggregates, are often used in literature. Unless otherwise stated, the term microparticle is a general reference to all of these species. Increasingly, microparticles are recognized as important means of intercellular communication in physiologic, pathophysiologic and apoptotic circumstances. While the contents of different types of microparticles vary with cell type, they can include nuclear, cytosolic and membrane proteins, as well as lipids and messenger and micro RNAs. Information regarding the state of the cell type of origin can be derived from an examination of microparticle contents. Thus, microparticles represent an unique window in real-time into the activities of cells, tissues and organs that may otherwise be difficult to sample.

A high proportion of adverse pregnancy outcomes have their pathophysiologic origins at the utero-placental interface in early pregnancy (Romero et al., supra, 2014; Gagnon, Eur J Obstet Gynecol Reprod Biol, 110:S99-S107, 2003; and Masoura et al., J. Obstet Gynaecol, 32:609-616, 2012). The ability to assess the state of associated tissue and cell populations is expected to be predictive of impending complications. Noninvasive tools for discriminating between pregnancies delivering at gestational ages marked by considerable neonatal morbidity (<34 weeks) compared with those delivering at term are particularly desirable given that timely administration of therapeutic agents may prevent preterm labor or otherwise prolong pregnancy.

Much needed are tools for determining whether a pregnant subject is at an increased risk for premature delivery, as well as tools for decreasing a pregnant subject's risk for premature delivery.

Patents, patent applications, patent application publications, journal articles and protocols referenced herein are incorporated by reference.

BRIEF SUMMARY OF THE INVENTION

The present disclosure relates to proteomic biomarkers of spontaneous preterm birth, proteomic biomarkers of term birth, and methods of use thereof. In particular, the present disclosure provides tools for determining whether a pregnant subject is at an increased risk for premature delivery, as well as tools for decreasing a pregnant subject's risk for premature delivery.

In one aspect, provided herein is a method for assessing risk of spontaneous preterm birth for a pregnant subject, the method comprising: (a) preparing a microparticle-enriched fraction from a blood sample from the pregnant subject; (b) determining a quantitative measure of a panel of microparticle-associated proteins in the fraction, wherein the panel comprises at least three proteins selected from the proteins of Table 1 or Table 2; and (c) assessing the risk of spontaneous preterm birth based on the measure. In some embodiments, the panel comprises at least three proteins selected from the proteins of Table 4. In some embodiments, the panel comprises at least three proteins selected from the proteins of Table 5. In some embodiments, the panel comprises at least three proteins selected from the triplexes of Table 7. In some embodiments, the panel comprises at least three proteins selected from the triplexes of Table 8. In some embodiments, the panel comprises at least three proteins selected from the group consisting of FETUB, CBPN, CHLE, C9, F13B, HEMO, IC1, PROS and TRFE. In some embodiments, the panel comprises at least three proteins selected from the group consisting of KLKB1, APOM, ITIH4, IC1, KNG1, C9, APOL1, PGRP2, THBG, FBLN1, ITIH2, VTDB, C8A, APOA1, HPT, and TRY3. In some embodiments, the panel comprises at least three proteins selected from the group consisting of AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1. In some embodiments, the panel comprises at least three proteins selected from the group consisting of A1AG1, A2MG, CHLE, IC1, KLKB1, and TRFE. In some embodiments, the panel comprises at least three proteins selected from the group consisting of F13A, IC1, PGRP2, and THBG. In some embodiments, the panel comprises at least three proteins selected from the group consisting of AACT, A1AG1, A2MG, CBPN, CHLE, C9, F13B, HEMO, IC1, KLKB1, LCAT, PGRP2, PROS, TRFE, A2AP, A2GL, APOL1, APOM, C6, CPN2, FBLN1, ITIH4, KAIN, KNG1, MBL2, SEPP1, THBG, TRY3, AMBP, APOA1, CDSL, C8A, F13A, HPT, ITIH1, and ITIH2. In some embodiments, the panel comprises at least three proteins selected from the group consisting of AACT, A1AG1, A2MG, CBPN, CHLE, C9, F13B, HEMO, IC1, KLKB1, LCAT, PGRP2, PROS, and TRFE. In some embodiments, the panel comprises at least three proteins selected from the group consisting of A2AP, A2GL, APOL1, APOM, C6, CPN2, FBLN1, ITIH4, KAIN, KNG1, MBL2, SEPP1, THBG, and TRY3. In some embodiments, panel comprises at least three proteins selected from the group consisting of AMBP, APOA1, CDSL, C8A, F13A, HPT, ITIH1, and ITIH2. In some embodiments, the panel comprises at least HEMO, KLKB1, and TRFE. In some embodiments, the panel comprises at least A2MG, HEMO, and MBL2. In some embodiments, the panel comprises at least KLKB1, IC1, and TRFE. In some embodiments, the panel comprises at least F13A, IC1, PGRP2, and THBG. In some embodiments, the panel comprises at least IC1, PGRP2, and THBG. In some embodiments, the panel comprises at least CHLE, FETUB, and PROS. In some embodiments, the panel comprises at least 4 proteins from Table 1, at least 4 proteins from Table 2, at least 4 proteins from Table 4, or at least 4 proteins from Table 5. In some embodiments, the panel comprises at least 5 proteins from Table 1, at least 5 proteins from Table 2, at least 5 proteins from Table 4, or at least 5 proteins from Table 5. In some embodiments, the panel comprises at least 6 proteins from Table 1, at least 6 proteins from Table 2, at least 6 proteins from Table 4, or at least 6 proteins from Table 5. In some embodiments, the panel comprises at least 7 proteins from Table 1, at least 7 proteins from Table 2, at least 7 proteins from Table 4, or at least 7 proteins from Table 5. In some embodiments, the panel comprises at least 8 proteins from Table 1, at least 8 proteins from Table 2, at least 8 proteins from Table 4, or at least 8 proteins from Table 5. In some embodiments, the panel comprises at least 3, at least 4, at least 5, at least 6, at least 7, or at least 8 proteins selected from FETUB, CBPN, CHLE, C9, F13B, HEMO, IC1, PROS and TRFE. In some embodiments, the panel comprises at least 3, at least 4, at least 5, at least 6, at least 7, or at least 8 proteins selected from KLKB1, APOM, ITIH4, IC1, KNG1, C9, APOL1, PGRP2, THBG, FBLN1, ITIH2, VTDB, C8A, APOA1, HPT, and TRY3. In some embodiments, the panel comprises at least 3, at least 4, at least 5, at least 6, at least 7, or at least 8 proteins selected from AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1. In some embodiments, the panel comprises at least 3, at least 4, at least 5, at least 6, at least 7, or at least 8 proteins selected from AACT, A1AG1, A2MG, CBPN, CHLE, C9, F13B, HEMO, IC1, KLKB1, LCAT, PGRP2, PROS, TRFE, A2AP, A2GL, APOL1, APOM, C6, CPN2, FBLN1, ITIH4, KAIN, KNG1, MBL2, SEPP1, THBG, TRY3, AMBP, APOA1, CDSL, C8A, F13A, HPT, ITIH1, and ITIH2. In some embodiments, the panel comprises at least 3, at least 4, at least 5, at least 6, at least 7, or at least 8 proteins selected from AACT, A1AG1, A2MG, CBPN, CHLE, C9, F13B, HEMO, IC1, KLKB1, LCAT, PGRP2, PROS, and TRFE. In some embodiments, the panel comprises at least 3, at least 4, at least 5, at least 6, at least 7, or at least 8 proteins selected from A2AP, A2GL, APOL1, APOM, C6, CPN2, FBLN1, ITIH4, KAIN, KNG1, MBL2, SEPP1, THBG, and TRY3. In some embodiments, the panel comprises at least 3, at least 4, at least 5, at least 6, or at least 7 proteins selected from AMBP, APOA1, CDSL, C8A, F13A, HPT, ITIH1, and ITIH2. In some embodiments, the panel comprises at least five proteins selected from A1AG1, A2MG, CHLE, IC1, KLKB1, and TRFE. In some embodiments, the panel comprises at least 4 or at least 5 proteins A1AG1, A2MG, CHLE, IC1, KLKB1, and TRFE. In some embodiments, the panel comprises any one of the five to eight plex multimarker panels presented in Table 9. In some embodiments, the panel comprises a first trimester panel. In some embodiments, the panel comprises a second trimester panel. In some embodiments, the panel comprises a 8-14 week panel. In some embodiments, the panel comprises a 18-24 week panel. In some embodiments, the panel comprises a 10-12 week panel. In some embodiments, the panel comprises a 22-24 week panel. In some embodiments, the pregnant subject is a primigravida female. In some embodiments, the sample is taken from the pregnant subject during the first trimester. In some embodiments, the sample is taken from the pregnant subject within 10 to 12 weeks of gestation. In some embodiments, the sample is taken from the pregnant subject during the second trimester. In some embodiments, the sample is taken from the pregnant subject within 18 to 24 weeks of gestation. In some embodiments, the steps of the method are carried out on a first sample taken from the pregnant subject during the first trimester, the steps of the method are repeated on a second sample taken from the pregnant subject during the second trimester. In some embodiments, a first sample is taken from the pregnant subject within 8 to 12 weeks of gestation and a second sample is taken from the pregnant subject within 18 to 24 weeks of gestation. In some embodiments, at least five markers are measured in both the first and second samples, and wherein the at least five markers selected from AACT, KLKB1, APOM, ITIH4, IC1, KNG1, C9, F13B, APOL1, LCAT, PGRP2, FBLN1, ITIH2, CD5L, CBPN, VTDB, AMBP, CBA, ITIH1, TTHY, and APOA1 are measured. In some embodiments, the blood sample is a serum or plasma sample. In some embodiments, the blood sample is plasma. In some embodiments, the blood sample is serum. In some embodiments, the microparticle-enriched fraction is prepared using size-exclusion chromatography. In some embodiments, the size-exclusion chromatography comprises elution with water. In some embodiments, the size-exclusion chromatography is performed with an agarose solid phase and an aqueous liquid phase. In some embodiments, the preparing step further comprises using ultrafiltration or reverse-phase chromatography. In some embodiments, the preparing step further comprises denaturation using urea, reduction using dithiothreitol, alkylation using iodoacetamine, and digestion using trypsin prior to the size exclusion chromatography. In some embodiments, determining a quantitative measure comprises mass spectrometry. In some embodiments, determining a quantitative measure comprises liquid chromatography/mass spectrometry (LC/MS). In some embodiments, the mass spectrometry comprises multiple reaction monitoring, the liquid chromatography is done using a solvent comprising acetonitrile, and/or the detecting step comprises assigning an indexed retention time to the proteins. In some embodiments, the mass spectrometry comprises multiple reaction monitoring. In some embodiments, the determining comprises executing a classification rule, which rule classifies the subject at being at risk of spontaneous preterm birth, and wherein execution of the classification rule produces a correlation between preterm birth or term birth with a p value of less than at least 0.05. In some embodiments, the determining comprises executing a classification rule, which rule classifies the subject at being at risk of spontaneous preterm birth, and wherein execution of the classification rule produces a receiver operating characteristic (ROC) curve, wherein the ROC curve has an area under the curve (AUC) of at least 0.6. In some embodiments, values on which the classification rule classifies a subject further include at least one of: maternal age, maternal body mass index, primiparous, and smoking during pregnancy. In some embodiments, the classification rule employs cut-off, linear regression (e.g., multiple linear regression (MLR), partial least squares (PLS) regression, principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (e.g., support vector machines). In some embodiments, the classification rule is configured to have a specificity of at least 80%, at least 90% or at least 95%. In some embodiments, the determining comprises determining whether the protein is above or below a threshold level. In some embodiments, the determining comprises comparing the measure of each protein in the panel to a reference standard. In some embodiments, the method further comprises communicating the risk of spontaneous preterm birth for a pregnant subject to a health care provider, wherein the communication informs a subsequent treatment decision for the pregnant subject. In some embodiments, the treatment is selected from the group consisting of a hormone and a corticosteroid. In some embodiments, the treatment comprises vaginal progesterone or parenteral 17-alpha-hydroxyprogesterone caproate. In some embodiments, the method further comprises a treatment step. In some embodiments, the treatment is selected from the group consisting of a hormone and a corticosteroid. In some embodiments, the treatment comprises vaginal progesterone or parenteral 17-alpha-hydroxyprogesterone caproate. In some embodiments, provided herein is a method of decreasing risk of spontaneous preterm birth for a pregnant subject and/or reducing neonatal complications of spontaneous preterm birth, the method comprising: (a) assessing risk of spontaneous preterm birth for a pregnant subject according to any of the methods provided herein; and (b) administering a therapeutic agent to the subject in an amount effective to decrease the risk of spontaneous preterm birth and/or reduce neonatal complications of spontaneous preterm birth. In some embodiments, the therapeutic agent is selected from the group consisting of a hormone and a corticosteroid. In some embodiments, the therapeutic agent comprises vaginal progesterone or parenteral 17-alpha-hydroxyprogesterone caproate.

In another aspect provided herein, is a method comprising administering to a pregnant subject characterized as having a panel of microparticle-associated proteins indicative of an increased risk of spontaneous preterm birth, an effective amount of a treatment designed to reduce the risk of spontaneous preterm birth, wherein the panel comprises at least three proteins selected from the proteins of Table 1 or Table 2. In some embodiments, the panel comprises at least three proteins selected from the proteins of Table 4. In some embodiments, the panel comprises at least three proteins selected from the proteins of Table 5. In some embodiments, the panel comprises at least three proteins selected from the triplexes of Table 7. In some embodiments, the panel comprises at least three proteins selected from the triplexes of Table 8. In some embodiments, the panel comprises at least three proteins selected from the group consisting of FETUB, CBPN, CHLE, C9, F13B, HEMO, IC1, PROS and TRFE. In some embodiments, the panel comprises at least three proteins selected from the group consisting of KLKB1, APOM, ITIH4, IC1, KNG1, C9, APOL1, PGRP2, THBG, FBLN1, ITIH2, VTDB, C8A, APOA1, HPT, and TRY3. In some embodiments, the panel comprises at least three proteins selected from the group consisting of AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1. In some embodiments, the panel comprises at least three proteins selected from the group consisting of A1AG1, A2MG, CHLE, IC1, KLKB1, and TRFE. In some embodiments, the panel comprises at least three proteins selected from the group consisting of F13A, IC1, PGRP2, and THBG. In some embodiments, the panel comprises at least three proteins selected from the group consisting of AACT, A1AG1, A2MG, CBPN, CHLE, C9, F13B, HEMO, IC1, KLKB1, LCAT, PGRP2, PROS, TRFE, A2AP, A2GL, APOL1, APOM, C6, CPN2, FBLN1, ITIH4, KAIN, KNG1, MBL2, SEPP1, THBG, TRY3, AMBP, APOA1, CDSL, C8A, F13A, HPT, ITIH1, and ITIH2. In some embodiments, the panel comprises at least three proteins selected from the group consisting of AACT, A1AG1, A2MG, CBPN, CHLE, C9, F13B, HEMO, IC1, KLKB1, LCAT, PGRP2, PROS, and TRFE. In some embodiments, the panel comprises at least three proteins selected from the group consisting of A2AP, A2GL, APOL1, APOM, C6, CPN2, FBLN1, ITIH4, KAIN, KNG1, MBL2, SEPP1, THBG, and TRY3. In some embodiments, panel comprises at least three proteins selected from the group consisting of AMBP, APOA1, CDSL, C8A, F13A, HPT, ITIH1, and ITIH2. In some embodiments, the panel comprises at least HEMO, KLKB1, and TRFE. In some embodiments, the panel comprises at least A2MG, HEMO, and MBL2. In some embodiments, the panel comprises at least KLKB1, IC1, and TRFE. In some embodiments, the panel comprises at least F13A, IC1, PGRP2, and THBG. In some embodiments, the panel comprises at least IC1, PGRP2, and THBG. In some embodiments, the panel comprises at least CHLE, FETUB, and PROS. In some embodiments, the panel comprises at least 4 proteins from Table 1, at least 4 proteins from Table 2, at least 4 proteins from Table 4, or at least 4 proteins from Table 5. In some embodiments, the panel comprises at least 5 proteins from Table 1, at least 5 proteins from Table 2, at least 5 proteins from Table 4, or at least 5 proteins from Table 5. In some embodiments, the panel comprises at least 6 proteins from Table 1, at least 6 proteins from Table 2, at least 6 proteins from Table 4, or at least 6 proteins from Table 5. In some embodiments, the panel comprises at least 7 proteins from Table 1, at least 7 proteins from Table 2, at least 7 proteins from Table 4, or at least 7 proteins from Table 5. In some embodiments, the panel comprises at least 8 proteins from Table 1, at least 8 proteins from Table 2, at least 8 proteins from Table 4, or at least 8 proteins from Table 5. In some embodiments, the panel comprises at least 3, at least 4, at least 5, at least 6, at least 7, or at least 8 proteins selected from FETUB, CBPN, CHLE, C9, F13B, HEMO, IC1, PROS and TRFE. In some embodiments, the panel comprises at least 3, at least 4, at least 5, at least 6, at least 7, or at least 8 proteins selected from KLKB1, APOM, ITIH4, IC1, KNG1, C9, APOL1, PGRP2, THBG, FBLN1, ITIH2, VTDB, C8A, APOA1, HPT, and TRY3. In some embodiments, the panel comprises at least 3, at least 4, at least 5, at least 6, at least 7, or at least 8 proteins selected from AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1. In some embodiments, the panel comprises at least 3, at least 4, at least 5, at least 6, at least 7, or at least 8 proteins selected from AACT, A1AG1, A2MG, CBPN, CHLE, C9, F13B, HEMO, IC1, KLKB1, LCAT, PGRP2, PROS, TRFE, A2AP, A2GL, APOL1, APOM, C6, CPN2, FBLN1, ITIH4, KAIN, KNG1, MBL2, SEPP1, THBG, TRY3, AMBP, APOA1, CDSL, C8A, F13A, HPT, ITIH1, and ITIH2. In some embodiments, the panel comprises at least 3, at least 4, at least 5, at least 6, at least 7, or at least 8 proteins selected from AACT, A1AG1, A2MG, CBPN, CHLE, C9, F13B, HEMO, IC1, KLKB1, LCAT, PGRP2, PROS, and TRFE. In some embodiments, the panel comprises at least 3, at least 4, at least 5, at least 6, at least 7, or at least 8 proteins selected from A2AP, A2GL, APOL1, APOM, C6, CPN2, FBLN1, ITIH4, KAIN, KNG1, MBL2, SEPP1, THBG, and TRY3. In some embodiments, the panel comprises at least 3, at least 4, at least 5, at least 6, or at least 7 proteins selected from AMBP, APOA1, CDSL, C8A, F13A, HPT, ITIH1, and ITIH2. In some embodiments, the panel comprises at least five proteins selected from A1AG1, A2MG, CHLE, IC1, KLKB1, and TRFE. In some embodiments, the panel comprises at least 4 or at least 5 proteins A1AG1, A2MG, CHLE, IC1, KLKB1, and TRFE. In some embodiments, the panel comprises any one of the five to eight plex multimarker panels presented in Table 9. In some embodiments, the panel comprises a first trimester panel. In some embodiments, the panel comprises a second trimester panel. In some embodiments, the panel comprises a 8-14 week panel. In some embodiments, the panel comprises a 18-24 week panel. In some embodiments, the panel comprises a 10-12 week panel. In some embodiments, the panel comprises a 22-24 week panel. In some embodiments, the treatment is selected from the group consisting of a hormone and a corticosteroid. In some embodiments, the treatment comprises vaginal progesterone or parenteral 17-alpha-hydroxyprogesterone caproate.

In another aspect, provided herein is a method comprising: (a) preparing a microparticle-enriched fraction from a blood sample from the pregnant subject; and (b) determining a quantitative measure of a panel of microparticle-associated proteins in the fraction, wherein the panel comprises at least three proteins selected from the proteins of Table 1 or Table 2. In some embodiments, the panel comprises at least three proteins selected from the proteins of Table 4. In some embodiments, the panel comprises at least three proteins selected from the proteins of Table 5. In some embodiments, the panel comprises at least three proteins selected from the triplexes of Table 7. In some embodiments, the panel comprises at least three proteins selected from the triplexes of Table 8. In some embodiments, the panel comprises at least three proteins selected from the group consisting of FETUB, CBPN, CHLE, C9, F13B, HEMO, IC1, PROS and TRFE. In some embodiments, the panel comprises at least three proteins selected from the group consisting of KLKB1, APOM, ITIH4, IC1, KNG1, C9, APOL1, PGRP2, THBG, FBLN1, ITIH2, VTDB, C8A, APOA1, HPT, and TRY3. In some embodiments, the panel comprises at least three proteins selected from the group consisting of AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1. In some embodiments, the panel comprises at least three proteins selected from the group consisting of A1AG1, A2MG, CHLE, IC1, KLKB1, and TRFE. In some embodiments, the panel comprises at least three proteins selected from the group consisting of F13A, IC1, PGRP2, and THBG. In some embodiments, the panel comprises at least three proteins selected from the group consisting of AACT, A1AG1, A2MG, CBPN, CHLE, C9, F13B, HEMO, IC1, KLKB1, LCAT, PGRP2, PROS, TRFE, A2AP, A2GL, APOL1, APOM, C6, CPN2, FBLN1, ITIH4, KAIN, KNG1, MBL2, SEPP1, THBG, TRY3, AMBP, APOA1, CDSL, C8A, F13A, HPT, ITIH1, and ITIH2. In some embodiments, the panel comprises at least three proteins selected from the group consisting of AACT, A1AG1, A2MG, CBPN, CHLE, C9, F13B, HEMO, IC1, KLKB1, LCAT, PGRP2, PROS, and TRFE. In some embodiments, the panel comprises at least three proteins selected from the group consisting of A2AP, A2GL, APOL1, APOM, C6, CPN2, FBLN1, ITIH4, KAIN, KNG1, MBL2, SEPP1, THBG, and TRY3. In some embodiments, panel comprises at least three proteins selected from the group consisting of AMBP, APOA1, CDSL, C8A, F13A, HPT, ITIH1, and ITIH2. In some embodiments, the panel comprises at least HEMO, KLKB1, and TRFE. In some embodiments, the panel comprises at least A2MG, HEMO, and MBL2. In some embodiments, the panel comprises at least KLKB1, IC1, and TRFE. In some embodiments, the panel comprises at least F13A, IC1, PGRP2, and THBG. In some embodiments, the panel comprises at least IC1, PGRP2, and THBG. In some embodiments, the panel comprises at least CHLE, FETUB, and PROS. In some embodiments, the panel comprises at least 4 proteins from Table 1, at least 4 proteins from Table 2, at least 4 proteins from Table 4, or at least 4 proteins from Table 5. In some embodiments, the panel comprises at least 5 proteins from Table 1, at least 5 proteins from Table 2, at least 5 proteins from Table 4, or at least 5 proteins from Table 5. In some embodiments, the panel comprises at least 6 proteins from Table 1, at least 6 proteins from Table 2, at least 6 proteins from Table 4, or at least 6 proteins from Table 5. In some embodiments, the panel comprises at least 7 proteins from Table 1, at least 7 proteins from Table 2, at least 7 proteins from Table 4, or at least 7 proteins from Table 5. In some embodiments, the panel comprises at least 8 proteins from Table 1, at least 8 proteins from Table 2, at least 8 proteins from Table 4, or at least 8 proteins from Table 5. In some embodiments, the panel comprises at least 3, at least 4, at least 5, at least 6, at least 7, or at least 8 proteins selected from FETUB, CBPN, CHLE, C9, F13B, HEMO, IC1, PROS and TRFE. In some embodiments, the panel comprises at least 3, at least 4, at least 5, at least 6, at least 7, or at least 8 proteins selected from KLKB1, APOM, ITIH4, IC1, KNG1, C9, APOL1, PGRP2, THBG, FBLN1, ITIH2, VTDB, C8A, APOA1, HPT, and TRY3. In some embodiments, the panel comprises at least 3, at least 4, at least 5, at least 6, at least 7, or at least 8 proteins selected from AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1. In some embodiments, the panel comprises at least 3, at least 4, at least 5, at least 6, at least 7, or at least 8 proteins selected from AACT, A1AG1, A2MG, CBPN, CHLE, C9, F13B, HEMO, IC1, KLKB1, LCAT, PGRP2, PROS, TRFE, A2AP, A2GL, APOL1, APOM, C6, CPN2, FBLN1, ITIH4, KAIN, KNG1, MBL2, SEPP1, THBG, TRY3, AMBP, APOA1, CDSL, C8A, F13A, HPT, ITIH1, and ITIH2. In some embodiments, the panel comprises at least 3, at least 4, at least 5, at least 6, at least 7, or at least 8 proteins selected from AACT, A1AG1, A2MG, CBPN, CHLE, C9, F13B, HEMO, IC1, KLKB1, LCAT, PGRP2, PROS, and TRFE. In some embodiments, the panel comprises at least 3, at least 4, at least 5, at least 6, at least 7, or at least 8 proteins selected from A2AP, A2GL, APOL1, APOM, C6, CPN2, FBLN1, ITIH4, KAIN, KNG1, MBL2, SEPP1, THBG, and TRY3. In some embodiments, the panel comprises at least 3, at least 4, at least 5, at least 6, or at least 7 proteins selected from AMBP, APOA1, CDSL, C8A, F13A, HPT, ITIH1, and ITIH2. In some embodiments, the panel comprises at least five proteins selected from A1AG1, A2MG, CHLE, IC1, KLKB1, and TRFE. In some embodiments, the panel comprises at least 4 or at least 5 proteins A1AG1, A2MG, CHLE, IC1, KLKB1, and TRFE. In some embodiments, the panel comprises any one of the five to eight plex multimarker panels presented in Table 9. In some embodiments, the panel comprises a first trimester panel. In some embodiments, the panel comprises a second trimester panel. In some embodiments, the panel comprises a 8-14 week panel. In some embodiments, the panel comprises a 18-24 week panel. In some embodiments, the panel comprises a 10-12 week panel. In some embodiments, the panel comprises a 22-24 week panel.

In another aspect, provided here is a method for assessing risk of spontaneous preterm birth for a pregnant subject, the method comprising: (a) preparing a microparticle-enriched fraction from a blood sample from the pregnant subject; (b) detecting a level of one or more proteins in the fraction, wherein the one or more proteins comprise one or more of CHLE, FETUB, and PROS; and (c) determining that the pregnant subject is at an increased risk of spontaneous preterm birth when the level of one or more proteins of a preterm birth group consisting of FETUB and PROS is above a threshold level, and/or when the level of one or more proteins of a term birth group consisting of CHLE is below a threshold level; or determining that the pregnant subject is at not at an increased risk of spontaneous preterm birth when the level of one or more proteins of the preterm birth group consisting of FETUB and PROS is below a threshold level, and/or when the level of one or more of proteins of the term birth group consisting of CHLE is above a threshold level. In some embodiments, the method further comprises (b2) detecting a level of one or more further proteins in the fraction from the pregnant subject, wherein the one or more further proteins comprise one or more of CBPN, C9, F13B, HEMO, IC1, and TRFE; and (c2) determining that the pregnant subject is at an increased risk of spontaneous preterm birth when the level of one or more further proteins of a further preterm birth group consisting of HEMO and TRFE is above a threshold level, and/or when the level of one or more of further proteins of a further term birth group consisting of CBPN, C9, F13B, and IC1, is below a threshold level in the sample; or determining that the pregnant subject is at not at an increased risk of spontaneous preterm birth when the level of one or more proteins of the preterm birth group consisting of HEMO and TRFE is below a threshold level, and/or when the level of one or more of proteins of the term birth group consisting of CBPN, C9, F13B, and IC1, is above a threshold level. In some embodiments, the detecting step comprises detecting the level of at least 4, 5, 6, 7 or 8 of the proteins in the fraction. In some embodiments, the pregnant subject is a primigravida female. In some embodiments, the sample is taken from the pregnant subject during the first trimester. In some embodiments, the ample is taken from the pregnant subject within 10 to 12 weeks of gestation. In some embodiments, the blood sample is a serum or plasma sample. In some embodiments, the microparticle-enriched fraction is prepared using size-exclusion chromatography with an agarose solid phase and an aqueous liquid phase. In some embodiments, the preparing step further comprises using ultrafiltration or reverse-phase chromatography. In some embodiments, the preparing step further comprises denaturation using urea, reduction using dithiothreitol, alkylation using iodoacetamine, and digestion using trypsin prior to the size exclusion chromatography. In some embodiments, the detecting step comprises liquid chromatography/mass spectrometry (LC/MS). In some embodiments, the mass spectrometry comprises multiple reaction monitoring, the liquid chromatography is done using a solvent comprising acetonitrile, and/or the detecting step comprises assigning an indexed retention time to the proteins. In some embodiments, the above claims, further comprising communicating the risk of spontaneous preterm birth for a pregnant subject to a health care provider, and optionally wherein the communication informs a subsequent treatment decision for the pregnant subject.

In another aspect, provided herein is a method for assessing risk of spontaneous preterm birth for a pregnant subject, the method comprising: (a) preparing a microparticle-enriched fraction from a blood sample from the pregnant subject; (b) detecting a level of one or more proteins in the fraction, wherein the one or more proteins comprise one or more of A2GL, AACT, BTD, C1QA, CFAD, CFAI, CHLE, CLUS, F9, F10, F13A, FCN3, FETUB, GPX3, HBA, HBB, HBD, HEP2, IGHG1, IGHG3, KAIN, LCAT, MASP1, MBL2, PGRP2, PLF4, PON1, PRG4, PROS, SEPP1, TRY3, and ZPI; and (c) determining that the pregnant subject is at an increased risk of spontaneous preterm birth when the level of one or more proteins of a preterm birth group consisting of C1QA, CFAD, CFAI, F9, FETUB, HBA, HBB, HBD, IGHG1, IGHG3, PLF4, PRG4, and PROS, is above a threshold level, and/or when the level of one or more proteins of a term birth group consisting of A2GL, AACT, BTD, CHLE, CLUS, F10, F13A, FCN3, GPX3, HEP2, KAIN, LCAT, MASP1, MBL2, PGRP2, PON1, SEPP1, TRY3, and ZPI, is below a threshold level; or determining that the pregnant subject is at not at an increased risk of spontaneous preterm birth when the level of one or more proteins of the preterm birth group consisting of C1QA, CFAD, CFAI, F9, FETUB, HBA, HBB, HBD, IGHG1, IGHG3, PLF4, PRG4, and PROS, is below a threshold level, and/or when the level of one or more of proteins of the term birth group consisting of A2GL, AACT, BTD, CHLE, CLUS, F10, F13A, FCN3, GPX3, HEP2, KAIN, LCAT, MASP1, MBL2, PGRP2, PON1, SEPP1, TRY3, and ZPI, is above a threshold level. In some embodiments the method further comprises (b2) detecting a level of one or more further proteins in the fraction from the pregnant subject, wherein the one or more further proteins comprise one or more of ANGT, APOA4, APOC3, APOE, C6, C8G, CBG, F13B, FIBA, HABP2, PLMN, THBG, and THRB; and (c2) determining that the pregnant subject is at an increased risk of spontaneous preterm birth when the level of one or more further proteins of a further preterm birth group consisting of ANGT, APOC3, APOE, CBG, and PLMN, is above a threshold level, and/or when the level of one or more of further proteins of a further term birth group consisting of APOA4, C6, C8G, F13B, FIBA, HABP2, THBG, and THRB, is below a threshold level in the sample; or determining that the pregnant subject is at not at an increased risk of spontaneous preterm birth when the level of one or more proteins of the preterm birth group consisting of ANGT, APOC3, APOE, CBG, and PLMN, is below a threshold level, and/or when the level of one or more of proteins of the term birth group consisting of APOA4, C6, CBG, F13B, FIBA, HABP2, THBG, and THRB, is above a threshold level. In some embodiments, the method further comprises (b3) detecting a level of one or more still further proteins in the fraction from the pregnant subject, wherein the one or more further proteins comprise one or more of A1AG1, A1AG2, A1AT, A1BG, A2MG, AMBP, ANT3, APOA1, APOB, APOD, APOH, APOL1, APOM, ATRN, C1QC, C1R, C1S, C4BPA, C8A, C9, CDSL, CERU, CFAB, CPN1, CPN2, F12, FBLN1, FETUA, FINC, HEMO, HPT, HPTR, IC1, IGHA2, IGJ, ITIH1, ITIH2, ITIH4, KLKB1, KNG1, LG3BP, SAA4, TRFE, TSP1, TTHY, VTDB, VTNC, and ZA2G; and (c3) determining that the pregnant subject is at an increased risk of spontaneous preterm birth when the level of one or more further proteins of a further preterm birth group consisting of APOB, APOH, C1S, C4BPA, CERU, HEMO, IGHA2, LG3BP, SAA4, TRFE, TSP1, and VTNC, is above a threshold level, and/or when the level of one or more of further proteins of a further term birth group consisting of A1AG1, A1AG2, A1AT, A1BG, A2MG, AMBP, ANT3, APOA1, APOD, APOL1, APOM, ATRN, C1QC, C1R, C8A, C9, CDSL, CFAB, CPN1, CPN2, F12, FBLN1, FETUA, FINC, HPT, HPTR, IC1, IGJ, ITIH1, ITIH2, ITIH4, KLKB1, KNG1, TTHY, VTDB, and ZA2G, is below a threshold level in the sample; or determining that the pregnant subject is at not at an increased risk of spontaneous preterm birth when the level of one or more proteins of the preterm birth group consisting of APOB, APOH, C1S, C4BPA, CERU, HEMO, IGHA2, LG3BP, SAA4, TRFE, TSP1, and VTNC, is below a threshold level, and/or when the level of one or more of proteins of the term birth group consisting of A1AG1, A1AG2, A1AT, A1BG, A2MG, AMBP, ANT3, APOA1, APOD, APOL1, APOM, ATRN, C1QC, C1R, C8A, C9, CDSL, CFAB, CPN1, CPN2, F12, FBLN1, FETUA, FINC, HPT, HPTR, IC1, IGJ, ITIH1, ITIH2, ITIH4, KLKB1, KNG1, TTHY, VTDB, and ZA2G, is above a threshold level. In some embodiments, the detecting step comprises detecting the level of three or more proteins in the fraction from the pregnant subject, wherein the three or more proteins are selected from the group consisting of CBPN, CHLE, C9, F13B, HEMO, ICI, PROS, and TRFE. In some embodiments, the detecting step comprises detecting the level of at least 4, 5, 6, 7 or 8 of the proteins in the fraction. In some embodiments, the pregnant subject is a primigravida female. In some embodiments, the sample is taken from the pregnant subject during the first trimester. In some embodiments, the ample is taken from the pregnant subject within 10 to 12 weeks of gestation. In some embodiments, the blood sample is a serum or plasma sample. In some embodiments, the microparticle-enriched fraction is prepared using size-exclusion chromatography with an agarose solid phase and an aqueous liquid phase. In some embodiments, the preparing step further comprises using ultrafiltration or reverse-phase chromatography. In some embodiments, the preparing step further comprises denaturation using urea, reduction using dithiothreitol, alkylation using iodoacetamine, and digestion using trypsin prior to the size exclusion chromatography. In some embodiments, the detecting step comprises liquid chromatography/mass spectrometry (LC/MS). In some embodiments, the mass spectrometry comprises multiple reaction monitoring, the liquid chromatography is done using a solvent comprising acetonitrile, and/or the detecting step comprises assigning an indexed retention time to the proteins. In some embodiments, the above claims, further comprising communicating the risk of spontaneous preterm birth for a pregnant subject to a health care provider, and optionally wherein the communication informs a subsequent treatment decision for the pregnant subject.

In another aspect, provided herein is a method of decreasing risk of spontaneous preterm birth for a pregnant subject and/or reducing neonatal complications of spontaneous preterm birth, the method comprising: assessing risk of spontaneous preterm birth for a pregnant subject according to the methods presented herein, and administering a therapeutic agent to the subject in an amount effective to decrease the risk of spontaneous preterm birth and/or reduce neonatal complications of spontaneous preterm birth. In some embodiments, the therapeutic agent is selected from the group consisting of a hormone and a corticosteroid. In some embodiments, the therapeutic agent comprises vaginal progesterone or parenteral 17-alpha-hydroxyprogesterone caproate.

In another aspect, provided herein is a method comprising: a) preparing a microparticle-enriched fraction from plasma or serum of a pregnant subject at from 8 to 14 weeks of gestation; b) using selected reaction monitoring mass spectrometry, determining a quantitative measure of one or more proteins in the fraction, wherein the proteins are selected from the proteins of Tables 1, 2, 4, 5, 7, 8, or 9; and c) executing a classification rule of a classification system which rule, based on values including the quantitative measures, classifies the subject as being at risk of spontaneous preterm birth, wherein the classification system, in a receiver operating characteristic (ROC) curve, has an area under the curve (AUC) of at least 0.6. In some embodiments, the subject is at 10-12 weeks of gestation. In some embodiments, executing is performed by computer. In some embodiments, the microparticle-enriched fraction is enriched by size exclusion chromatography. In some embodiments, the size exclusion chromatography comprises elusion with water. In some embodiments, mass spectrometry comprises LC-MS. In some embodiments, values on which the classification rule classifies a subject further include at least one of: maternal age, maternal body mass index, primiparous, and smoking during pregnancy. In some embodiments, the classification system is a linear classification system. In some embodiments, the classification system employs cut-off, linear regression (e.g., multiple linear regression (MLR), partial least squares (PLS) regression, principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (e.g., support vector machines). In some embodiments, the classification rule is configured to have a specificity of at least 80%, at least 90% or at least 95%.

In another aspect provided herein is a method comprising: a) preparing a microparticle-enriched fraction from plasma or serum of a pregnant subject at from 8 to 14 weeks of gestation; b) using selected reaction monitoring mass spectrometry, determining a quantitative measure of one or more pairs proteins in the fraction, wherein the pairs are selected from the pairs of proteins of Table 6; and c) executing a classification rule which rule, based on values including the quantitative measures, classifies the subject as being at risk of spontaneous preterm birth, wherein the classification model produces a correlation between preterm birth or term birth with a p value of less than any of 0.07, 0.01, 0.005 or 0.001. In some embodiments, the subject is at 10-12 weeks of gestation. In some embodiments, executing is performed by computer. In some embodiments, the microparticle-enriched fraction is enriched by size exclusion chromatography. In some embodiments, the size exclusion chromatography comprises elusion with water. In some embodiments, mass spectrometry comprises LC-MS. In some embodiments, values on which the classification rule classifies a subject further include at least one of: maternal age, maternal body mass index, primiparous, and smoking during pregnancy. In some embodiments, the classification system is a linear classification system. In some embodiments, the classification system employs cut-off, linear regression (e.g., multiple linear regression (MLR), partial least squares (PLS) regression, principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (e.g., support vector machines). In some embodiments, the classification rule is configured to have a specificity of at least 80%, at least 90% or at least 95%.

In another aspect, provided herein is a method comprising: a) preparing a microparticle-enriched fraction from plasma or serum of a pregnant subject at from 8 to 14 weeks of gestation; b) using selected reaction monitoring mass spectrometry, determining a quantitative measure of a panel of proteins in the fraction, wherein the panel comprises at least three proteins selected from the triplexes of Table 7; and c) executing a classification rule of a classification system which rule, based on values including the quantitative measures, classifies the subject as being at risk of spontaneous preterm birth, wherein the classification system, in a receiver operating characteristic (ROC) curve, has an area under the curve (AUC) of at least 0.86. In some embodiments, the panel is a panel of Table 9. In some embodiments, the subject is at 10-12 weeks of gestation. In some embodiments, executing is performed by computer. In some embodiments, the microparticle-enriched fraction is enriched by size exclusion chromatography. In some embodiments, the size exclusion chromatography comprises elusion with water. In some embodiments, mass spectrometry comprises LC-MS. In some embodiments, values on which the classification rule classifies a subject further include at least one of: maternal age, maternal body mass index, primiparous, and smoking during pregnancy. In some embodiments, the classification system is a linear classification system. In some embodiments, the classification system employs cut-off, linear regression (e.g., multiple linear regression (MLR), partial least squares (PLS) regression, principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (e.g., support vector machines). In some embodiments, the classification rule is configured to have a specificity of at least 80%, at least 90% or at least 95%.

In another aspect, provided herein is a method comprising: a) preparing a microparticle-enriched fraction from plasma or serum of a pregnant subject at from 8 to 14 weeks of gestation; b) using selected reaction monitoring mass spectrometry, determining a quantitative measure of one or more proteins in the fraction, wherein the one or more proteins are selected from: i) proteins of the coagulation/wound healing pathway selected from: F13A, F13B, FBLN1, FA9, FA10, PROS, FIBA, FIBG, FINC, HABP2 and PLF4; ii) proteins of the inflammation/oxidative stress pathway selected from: CBPN, CHLE, HEMO, TRFE, VTDB, PGRP2, CD5L, SEPP1, CPN2, FETUA, FETUB, PON1, SAA4, GPX3; iii) proteins of the kinin-kallikrein-angiotensin system pathway selected from: AACT, KLKB1, KNG1, KAIN, HEP2; iv) proteins of the complement/adaptive immunity pathway selected from: IC1, C9, CBPN, C6, CBA, HPT, MBL2, A2GL, A1AG1, C7, ATRN, C1R, FCN3, HPTR, IGJ, MASP1, CBG, CLUS, A1AG2, A1BG; v) proteins of the fibrinolysis/anti-coagulation/itih related pathway selected from: ITIH1, ITIH2, ITIH4, AMBP, TRY3, A2AP, A2MG, A1AT, ZPI; vi) proteins of the lipid metabolism pathway selected from: APOM, APOL1, APOA1, LCAT, ZA2G, APOD, APOF; vii) proteins of the thyroid related pathway selected from: THBG, TTHY, THRB; and c) executing a classification rule which rule, based on values including the quantitative measures, classifies the subject as being at risk of pre-term birth. In some embodiments, the subject is at 10-12 weeks of gestation. In some embodiments, executing is performed by computer. In some embodiments, the microparticle-enriched fraction is enriched by size exclusion chromatography. In some embodiments, the size exclusion chromatography comprises elusion with water. In some embodiments, mass spectrometry comprises LC-MS. In some embodiments, values on which the classification rule classifies a subject further include at least one of: maternal age, maternal body mass index, primiparous, and smoking during pregnancy. In some embodiments, the classification system is a linear classification system. In some embodiments, the classification system employs cut-off, linear regression (e.g., multiple linear regression (MLR), partial least squares (PLS) regression, principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (e.g., support vector machines). In some embodiments, the classification rule is configured to have a specificity of at least 80%, at least 90% or at least 95%.

In another aspect, provided herein is a method of decreasing risk of spontaneous preterm birth and/or reducing neonatal complications, the method comprising: a) determining by any of the methods presented herein that a subject is at risk of spontaneous preterm birth; and b) administering to the subject a therapeutic agent in an amount effective to decrease the risk of spontaneous preterm birth and/or reduce neonatal complications.

In another aspect, provided herein is a method comprising: a) providing a microparticle-enriched fraction from plasma or serum of a plurality of pregnant subjects obtained at from 8 to 14 weeks of gestation, wherein the plurality of subjects include a plurality of subjects that subsequently experienced preterm birth and a plurality of subjects that subsequently experienced term birth; b) using selected reaction monitoring mass spectrometry, determining a quantitative measure of a plurality of proteins in the fraction, wherein the proteins are selected from: the proteins of Tables 1, 2, 4, 5, 7, 8, or 9; b) preparing a training data set indicating, for each sample, values indicating: (i) classification of the sample as belonging to preterm birth or term birth classes; and (ii) the quantitative measures of the plurality of protein biomarkers; and c) training a learning machine algorithm on the training data set, wherein training generates one or more classification rules that classify a sample as belonging to the preterm birth class or the term birth class. In some embodiments the training data set further comprises values indicating at least one of: (iii) subject status as maternal age, maternal body mass index, primiparous, and smoking during pregnancy. In some embodiments, further comprising choosing a model from among a plurality of models generated. In some embodiments, the model is chosen based on pre-selected criteria including sensitivity and specificity. In some embodiments, the classification rule is configured to have a sensitivity of at least 75%, at least 85% or at least 95%.

In another aspect provided herein is a computer readable medium in tangible, non-transitory form comprising code to implement a classification rule generated any of the methods presented herein.

In another aspect provided herein is a computer system comprising: (a) a processor; and (b) a memory, coupled to the processor, the memory storing a module comprising: (i) test data for a sample from a subject including values indicating a quantitative measure of a plurality of protein biomarkers in the fraction, wherein the proteins are selected from the proteins of Tables 1, 2, 4, 5, 7, 8, or 9; (ii) a classification rule which, based on values including the measurements, classifies the subject as being at risk of pre-term birth, wherein the classification rule is configured to have a sensitivity of at least 75%, at least 85% or at least 95%; and (iii) computer executable instructions for implementing the classification rule on the test data.

DETAILED DESCRIPTION OF THE INVENTION

Figure 1:
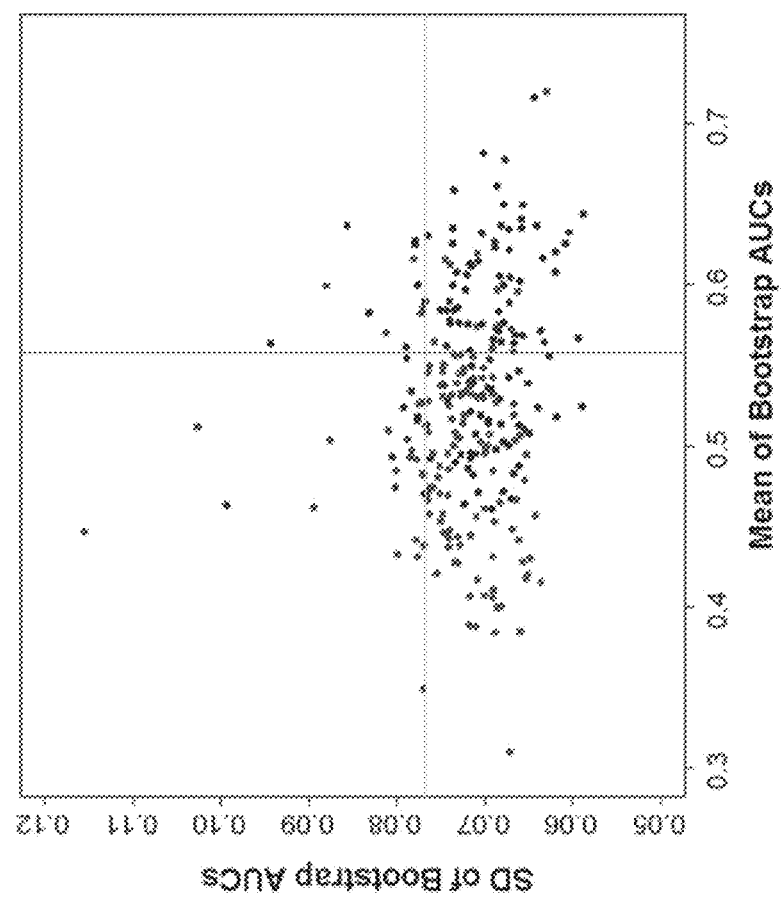
FIG. 1 is a graph of a bootstrap ROC analysis to select proteins for detection of SPTBs from term cases. Each protein was plotted as a blue-colored point with mean and SD of the AUCs from bootstrap ROC analysis as x- and y-axis values, correspondingly. Results from the same analysis yet with sample label permutation were plotted as red points. A total of 62 proteins (blue points) within the lower right quadrant bounded by the magenta vertical line (mean+SD of x-values of the red points) and the green horizontal line (mean+SD of y values of the blue points) were selected for their relatively stable and significant discriminatory power. In comparison, only 12 of proteins from label permutated analysis (red points) were in this quadrant. The estimated false discovery rate was therefore <20% (12/62).

This disclosure provides statistically significant CMP-associated (circulation microparticle-associated) protein biomarkers and multiplex panels associated with biological processes relevant to pregnancy that are already unique in their expression profiles at 10-12 weeks gestation among females who go on to deliver spontaneously at <38 weeks. These biomarkers are useful for the clinical stratification of patients at risk of SPTB well before clinical presentation. Such identification is indicative of a need for increased observation and may result in the application of prophylactic therapies, which together may significantly improve the management of these patients.

Protein Biomarkers

The present disclosure provides tools for assessing and decreasing risk of spontaneous preterm birth. The methods of the present disclosure include a step of detecting the level of at least one microparticle-associated protein in a biological sample.

A microparticle refers to an extracellular microvesicle or lipid raft protein aggregate having a hydrodynamic diameter of from about 50 to about 5000 nm. As such the term microparticle encompasses exosomes (about 50 to about 100 nm), microvesicles (about 100 to about 300 nm), ectosomes (about 50 to about 1000 nm), apoptotic bodies (about 50 to about 5000 nm) and lipid protein aggregates of the same dimensions. As used herein, the term "about" as used herein in reference to a value refers to 90 to 110% of that value. For instance a diameter of about 1000 nm is a diameter within the range of 900 nm to 1100 nm.

A microparticle-associated protein refers to a protein or fragment thereof (e.g., polypeptide) that is detectable in a microparticle-enriched sample from a mammalian (e.g., human) subject. As such a microparticle-associated protein is not restricted to proteins or fragments thereof that are physically associated with microparticles at the time of detection; the proteins or fragments may be incorporated between microparticles, or the proteins or fragments may have been associate with the microparticle at some earlier time prior to detection.

Unless otherwise stated, the term protein encompasses polypeptides and fragments thereof "Fragments" include polypeptides that are shorter in length than the full length or mature protein of interest. If the length of a protein is x amino acids, a fragment is x−1 amino acids of that protein. The fragment may be shorter than this (e.g., x−2, x−3, x−4, . . . ), and is preferably 100 amino acids or less (e.g., 90, 80, 70, 60, 50, 40, 30, 20 or 10 amino acids or less). The fragment may be as short as 4 amino acids, but is preferably longer (e.g., 5, 6, 7, 8, 9, 10, 12, 15, 20, 25, 30, 35, 40, 50, 60, 70, 80, 90, or 100 amino acids).

The present disclosure provides tools for detecting the level of at least one microparticle-associated protein. As used herein "detecting the level" of at least one microparticle-associated protein encompasses detecting the expression level of the protein, detecting the absolute concentration of the protein, detecting an increase or decrease of the protein level in relation to a reference standard, detecting an increase or decrease of the protein level in relation to a threshold level, measuring the protein concentration, quantifying the protein concentration, determining a quantitative measure, detecting the presence (e.g., level above a threshold or detectable level) or detecting the absence (e.g., level below a threshold or undetectable level) of at least one microparticle-associated protein in a sample from a pregnant subject. In some embodiments, the quantitative measure can be an absolute value, a ratio, an average, a median, or a range of numbers.

As used herein, "detection of a protein" and "determining a quantitative measure of one or more proteins" encompasses any means, including, detection by an MS method that detects fragments of a protein. The data disclosed in the tables and figures was obtained by MRM-MS, which detects proteins by selecting peptide fragments of a parent protein for detection.

During development of the present disclosure numerous microparticle-associated proteins were determined to be altered in samples from subjects having preterm births (as compared to samples from subjects have term births), and are therefore termed "preterm birth biomarkers." Additionally during development of the present disclosure numerous microparticle-associated proteins were determined to be not altered in samples from subjects having preterm births (as compared to samples from subjects have term births), and are therefore termed "term birth biomarkers."

In some embodiments, the methods of the present disclosure include a step of detecting the level of a panel of microparticle-associated proteins in a biological sample from a pregnant test subject, where the microparticle-associated proteins are from Table 1. In some embodiments, the methods of the present disclosure include a step of detecting the level of at least one microparticle-associated protein in a biological sample from a pregnant test subject, where the at least one protein is selected from Table 1. In some embodiments, the methods of the present disclosure include a step of detecting the level of at least two, at least three, at least four, at least five, at least six, at least seven, at least eight, at least nine, or at least ten microparticle-associated proteins in a biological sample from a pregnant test subject, where the at least one protein is selected from Table 1. In some embodiments, the methods of the present disclosure include a step of detecting the level of five, six, seven, eight, or nine microparticle-associated proteins in a biological sample from a pregnant test subject, where the proteins are selected from Table 1. In an exemplary embodiment, the methods of the present disclosure include a step of detecting the level of six microparticle-associated proteins in a biological sample from a pregnant test subject, where the six proteins are selected from Table 1. In an exemplary embodiment, the methods of the present disclosure include a step of detecting the level of seven microparticle-associated proteins in a biological sample from a pregnant test subject, where the seven proteins are selected from Table 1. In an exemplary embodiment, the methods of the present disclosure include a step of detecting the level of eight microparticle-associated proteins in a biological sample from a pregnant test subject, where the eight proteins are selected from Table 1. In an exemplary embodiment, the methods of the present disclosure include a step of detecting the level of nine microparticle-associated proteins in a biological sample from a pregnant test subject, where the nine proteins are selected from Table 1.

In some embodiments, if the sample is obtained at about 10-12 weeks gestation, the microparticle-associated protein can display the directionality (+ or −) indicated in the last column of Table 1. In the last column of Table 1, (−) indicates the biomarker is downregulated in SPTB cases versus TERM controls; and (+) indicates the biomarker is unregulated in SPTB cases vs TERM controls.

TABLE 1

Microparticle-Associated Proteins Differentially Expressed in Preterm Birth

| Symbol | Protein Name (Alternative Name) | UniProtKB | (+ or −) 10-12 wk |
|---|---|---|---|
| A1AG1 (ORM1) | Alpha-1-acid glycoprotein 1 (Orosomucoid-1) | P02763 | − |
| A1AG2 (ORM2) | Alpha-1-acid glycoprotein 2 (Orosomucoid-2) | P19652 | − |
| A1AT (SERPINA1) | Alpha-1-antitrypsin | P01009 | − |
| A1BG | Alpha-1B-glycoprotein | P04217 | − |
| A2AP (SERPINF2) | Alpha-2-antiplasmin | P08697 | |
| A2GL (LRG) | Leucine-rich alpha-2-glycoprotein | P02750 | − |
| A2MG (A2M) | Alpha-2-macroglobulin | P01023 | − |
| AACT (SERPINA3) | Alpha-1-antichymotrypsin | P01011 | − |
| AMBP | Alpha-1-microglobulin/bikunin precursor | P02760 | − |
| ANGT (SERPINA8) | Angiotensinogen | P01019 | + |
| ANT3 (SERPINC1) | Antithrombin-III | P01008 | − |
| APOA1 | Apolipoprotein A1 | P02647 | − |
| APOA4 | Apolipoprotein A1 | P06727 | − |
| APOB | Apolipoprotein B100 | P04114 | + |
| APOC3 | Apolipoprotein C3 | P02656 | + |
| APOD | Apolipoprotein D | P05090 | − |
| APOE | Apolipoprotein E | P02649 | + |
| APOH | Apolipoprotein H | P02749 | + |
| APOL1 | Apolipoprotein L1 | O14791 | − |
| APOM | Apolipoprotein M | O95445 | − |
| ATRN | Attractin | O75882 | |
| BTD | Biotinidase | P43251 | |
| C1QA | Complement C1q subunit A | P02745 | + |
| C1QC | Complement C1q subunit C | P02747 | − |
| C1R | Complement C1r | P00736 | |
| C1S | Complement C1s | P09871 | + |
| C4BPA | Complement C4b-binding protein alpha chain | P04003 | + |
| C6 | Complement C6 (CO6) | P13671 | − |
| C8A | Complement C8 alpha chain (CO8A) | P07357 | − |
| C8G | Complement C8 gamma chain (CO8G) | P07360 | − |
| C9 | Complement C9 (CO9) | P02748 | − |
| CBG (SERPINA6) | Corticosteroid-binding globulin | P08185 | + |
| CD5L | CD5 antigen-like | O43866 | − |
| CERU (CP) | Ceruloplasmin (Ferroxidase) | P00450 | + |
| CFAB (CFB) | Complement Factor B (C3/C5 convertase) | P00751 | − |
| CFAD (CFD) | Complement Factor D (Adipsin) | P00746 | + |
| CFAI (CFI) | Complement Factor I (C3B/C4B inact.) | P05156 | + |
| CHLE | Cholinesterase | P06276 | − |
| CLUS | Clusterin (Apolipoprotein J) | P10909 | − |
| CPN1 (CBPN) | Carboxypeptidase N, polypeptide 1 | P15169 | − |
| CPN2 | Carboxypeptidase N, polypeptide 2 | P22792 | − |
| F10 (FA10) | Coagulation factor X | P00742 | |
| F12 (FA12) | Coagulation factor XII | P00748 | − |
| F13A | Coagulation factor XIII A chain | P00488 | − |
| F13B | Coagulation factor XIII B chain | P05160 | − |
| F9 (FA9) | Coagulation factor IX | P00740 | + |
| FBLN1 | Fibulin 1 | P23142 | − |
| FCN3 | Ficolin-3 | O75636 | − |
| FETUA (AHSG) | Fetuin-A (Alpha-2-HS-glycoprotein) | P02765 | − |
| FETUB | Fetuin-B | Q9UGM5 | + |
| FIBA (FGA) | Fibrinogen alpha chain | P02671 | − |
| FINC (FN1) | Fibronectin 1 | P02751 | − |
| GPX3 | Glutathione peroxidase 3 | P22352 | − |
| HABP2 | Hyaluronan-binding protein 2 | Q14520 | − |
| HBA | Hemoglobin subunit alpha | P69905 | + |
| HBB | Hemoglobin subunit beta | P68871 | + |
| HBD | Hemoglobin subunit delta | P02042 | + |

TABLE 1-continued

Microparticle-Associated Proteins Differentially Expressed in Preterm Birth

| Symbol | Protein Name (Alternative Name) | UniProtKB | (+ or −) 10-12 wk |
|---|---|---|---|
| HEMO (HPX) | Hemopexin (Beta-1B-glycoprotein) | P02790 | + |
| HEP2 (SERPIND1) | Heparin cofactor 2 | P05546 | − |
| HPT (HP) | Haptoglobin | P00738 | − |
| HPTR (HPR) | Haptoglobin-related protein | P00739 | − |
| IC1 (SERPING1) | Plasma protease C1 inhibitor | P05155 | − |
| IGHA2 | Immunoglobulin Heavy Chain Alpha 2 | P01877 | + |
| IGHG1 | Immunoglobulin Heavy Chain Gamma 1 | P01857 | + |
| IGHG3 | Immunoglobulin Heavy Chain Gamma 3 | P01860 | + |
| IGJ | Immunoglobulin J Chain | P01591 | − |
| ITIH1 | Inter-alpha-trypsin inhibitor H1 | P19827 | − |
| ITIH2 | Inter-alpha-trypsin inhibitor H2 | P19823 | − |
| ITIH4 | Inter-alpha trypsin inhibitor H4 | Q14624 | − |
| KAIN (SERPINA4) | Kallistatin (Kallikrein inhibitor) | P29622 | − |
| KLKB1 | Kallikrein B1 (Plasma kallikrein) | P03952 | − |
| KNG1 | Kininogen-1 | P01042 | − |
| LCAT | Lecithin-cholesterol acyltransferase | P04180 | − |
| LG3BP (LGALS3BP) | Galectin-3-binding protein | Q08380 | + |
| MASP1 | Mannan-binding lectin serine protease 1 | P48740 | − |
| MBL2 | Mannose-binding protein C | P11226 | − |
| PGRP2 | N-acetylmuramoyl-L-alanine amidase | Q96PD5 | − |
| PLF4 (PF4) | Platelet factor 4 (Oncostatin-A, CXCL4) | P02776 | + |
| PLMN (PLG) | Plasminogen | P00747 | + |
| PON1 | Serum paraoxonase/arylesterase 1 | P27169 | − |
| PRG4 (MSF) | Proteoglycan 4 | Q92954 | + |
| PROS | Vitamin K-dependent protein S | P07225 | + |
| SAA4 | Serum amyloid A-4 protein | P35542 | + |
| SEPP1 (SELP) | Selenoprotein P | P49908 | − |
| THBG (SERPINA7) | Thyroxine-binding globulin | P05543 | − |
| THRB (F2) | Prothrombin | P00734 | − |
| TRFE (TF) | Serotransferrin (Transferrin, Siderophilin) | P02787 | + |
| TRY3 (PRSS3) | Trypsin-3 | P35030 | − |
| TSP1 (THBS1) | Thrombospondin-1 | P07996 | + |
| TTHY (TTR) | Transthyretin | P02766 | − |
| VTDB (GC) | Vitamin D-binding protein | P02774 | − |
| VTNC (VTN) | Vitronectin | P04004 | + |
| ZA2G(AZGP1) | Zinc-alpha-2-glycoprotein | P25311 | − |
| ZPI (SERPINA10) | Protein Z-dependent protease inhibitor | Q9UK55 | − |

In some embodiments, the methods of the present disclosure include a step of detecting the level of a panel of microparticle-associated proteins in a biological sample from a pregnant test subject, where the microparticle-associated proteins are from Table 2. In some embodiments, the methods of the present disclosure include a step of detecting the level of at least one microparticle-associated protein in a biological sample from a pregnant test subject, where the at least one protein is selected from Table 2. The proteins listed in Table 2 correspond to proteins with statistically consistent performance as differentiating SPTB from term controls. In some embodiments, the methods of the present disclosure include a step of detecting the level of at least two, at least three, at least four, at least five, at least six, at least seven, at least eight, at least nine, or at least ten microparticle-associated proteins in a biological sample from a pregnant test subject, where the at least one protein is selected from Table 2. In some embodiments, the methods of the present disclosure include a step of detecting the level of five, six, seven, eight, or nine microparticle-associated proteins in a biological sample from a pregnant test subject, where the proteins are selected from Table 2. In an exemplary embodiment, the methods of the present disclosure include a step of detecting the level of five microparticle-associated proteins in a biological sample from a pregnant test subject, where the five proteins are selected from Table 2. In an exemplary embodiment, the methods of the present disclosure include a step of detecting the level of six microparticle-associated proteins in a biological sample from a pregnant test subject, where the six proteins are selected from Table 2. In an exemplary embodiment, the methods of the present disclosure include a step of detecting the level of seven microparticle-associated proteins in a biological sample from a pregnant test subject, where the seven proteins are selected from Table 2. In an exemplary embodiment, the methods of the present disclosure include a step of detecting the level of eight microparticle-associated proteins in a biological sample from a pregnant test subject, where the eight proteins are selected from Table 2. In an exemplary embodiment, the methods of the present disclosure include a step of detecting the level of nine microparticle-associated proteins in a biological sample from a pregnant test subject, where the nine proteins are selected from Table 2.

TABLE 2

Microparticle-Associated Proteins Differentially Expressed in Preterm Birth

| Symbol | Protein Name (Alternative Name) | UniProtKB |
|---|---|---|
| A1AG1 (ORM1) | Alpha-1-acid glycoprotein 1 (Orosomucoid-1) | P02763 |
| A1AG2 (ORM2) | Alpha-1-acid glycoprotein 2 (Orosomucoid-2) | P19652 |
| A1AT | Alpha-1-antitrypsin | P01009 |
| A2AP | | |
| A2GL (LRG) | Leucine-rich alpha-2-glycoprotein | P02750 |
| A2MG (A2M) | Alpha-2-macroglobulin | P01023 |
| ABCF1 | ATP-binding cassette sub-family F member 1 | Q8NE71 |
| AFAM | Afamin | P43652 |
| ALBU | Albumin | P02768 |
| ANT3 (SERPINC1) | Antithrombin-III | P01008 |
| APOA1 | Apolipoprotein A1 | P02647 |
| APOA4 | Apolipoprotein A1 | P06727 |
| APOC2 | Apolipoprotein C2 | P02655 |
| APOC3 | Apolipoprotein C3 | P02656 |
| APOD | Apolipoprotein D | P05090 |
| APOF | Apolipoprotein F | Q13790 |
| APOL1 | Apolipoprotein L1 | O14791 |
| APOM | Apolipoprotein M | O95445 |
| ATRN | Attractin | O75882 |
| BGH3 | Transforming growth factor-beta induced protein ig-h3 | Q15582 |
| BTD | Biotinidase | P43251 |
| C1R | Complement C1r | P00736 |
| C1S | Complement C1s | P09871 |
| C3 | Complement Component 3 | P01024 |
| C4A | Complement Component 4A | P0C0L4 |
| C4BPA | Complement C4b-binding protein alpha chain | P04003 |
| C4BPB | C4b-binding protein beta chain | P20851 |
| C7 | Complement Component 7 (CO7) | P10643 |
| C8A | Complement C8 alpha chain | P07357 |
| C8B | Complement Component 8 beta chain | P07358 |
| C9 | Complement C9 (CO9) | P02748 |
| CERU (CP) | Ceruloplasmin (Ferroxidase) | P00450 |
| CFAD (CFD) | Complement Factor D (Adipsin) | P00746 |

TABLE 2-continued

Microparticle-Associated Proteins Differentially Expressed in Preterm Birth

| Symbol | Protein Name (Alternative Name) | UniProtKB |
|---|---|---|
| CFAH | Complement Factor H | P08603 |
| CFAI | Complement Factor H | P05156 |
| CXCL7 | Platelet basic protein | P02775 |
| ECM1 | Extracellular matrix protein 1 | Q16610 |
| F10 (FA10) | Coagulation factor X | P00742 |
| F12 (FA12) | Coagulation factor XII | P00748 |
| FBLN1 | Fibulin 1 | P23142 |
| FETUB | Fetuin-B | Q9UGM5 |
| FIBA (FGA) | Fibrinogen alpha chain | P02671 |
| FIBB | Fibrinogen beta chain | P02765 |
| FIBG | Fibrinogen gamma chain | P02679 |
| HABP2 | Hyaluronan-binding protein 2 | Q14520 |
| HBA | Hemoglobin subunit alpha | P69905 |
| HEMO (HPX) | Hemopexin (Beta-1B-glycoprotein) | P02790 |
| HEP2 (SERPIND1) | Heparin cofactor 2 | P05546 |
| HPT (HP) | Haptoglobin | P00738 |
| HRG | Histidine-rich glycoprotein | P04196 |
| IC1 (SERPING1) | Plasma protease C1 inhibitor | P05155 |
| IGHA1 | Ig alpha-1 chain C region | P01876 |
| IGHA2 | Ig alpha-2 chain C region | P01877 |
| IGHG1 | Immunoglobulin Heavy Chain Gamma 1 | P01857 |
| IGHG2 | Ig gamma-2 chain C region | P01859 |
| IGHG4 | Ig gamma-4 chain C region | P01861 |
| IGHM | Ig mu chain C region | P01871 |
| IPSP | Plasma serine protease inhibitor | P05154 |
| IT1H2 | Inter-alpha-trypsin inhibitor H2 | P19823 |
| ITIH4 | Inter-alpha-trypsin inhibitor heavy chain H4 | Q14624 |
| KAIN (SERPINA4) | Kallistatin (Kallikrein inhibitor) | P29622 |
| KLKB1 | Kallikrein B1 (Plasma kallikrein) | P03952 |
| KNG1 | Kininogen-1 | P01042 |
| MASP1 | Mannan-binding lectin serine protease 1 | P48740 |
| MBL2 | Mannose-binding protein C | P11226 |
| PEDF | Pigment epithelium-derived factor | P36955 |
| PGRP2 | N-acetylmuramoyl-L-alanine amidase | Q96PD5 |
| PLMN (PLG) | Plasminogen | P00747 |
| PRG4 (MSF) | Proteoglycan 4 | Q92954 |
| SAA4 | Serum amyloid A-4 protein | P35542 |
| SEPP1 (SELP) | Selenoprotein P | P49908 |
| TETN | Tetranectin | P05452 |
| THBG (SERPINA7) | Thyroxine-binding globulin | P05543 |
| TRFE (TF) | Serotransferrin (Transferrin, Siderophilin) | P02787 |
| TSP1 (THBS1) | Thrombospondin-1 | P07996 |
| VTDB (GC) | Vitamin D-binding protein | P02774 |
| VTNC (VTN) | Vitronectin | P04004 |
| VWF | Von Willebrand factor | P04275 |
| ZA2G (AZGP1) | Zinc-alpha-2-glycoprotein | P25311 |
| ZPI (SERPINA10) | Protein Z-dependent protease inhibitor | Q9UK55 |

In another embodiment, the methods of the present disclosure include a step of detecting the level of three proteins selected from the proteins of Table 1, Table 2, Table 4, Table 5, Table 7 or Table 8. In some embodiments, the at least 3 proteins comprise at least HEMO, KLKB1, and TRFE. In some embodiments, the at least 3 proteins comprise at least A2MG, HEMO, and MBL2. In some embodiments, the at least 3 proteins comprise at least KLKB1, IC1, and TRFE. In some embodiments, the at least 3 proteins comprise at least 3 proteins from F13A, IC1, PGRP2, and THBG. In some embodiments, the at least 3 proteins comprise at least IC1, PGRP2, and THBG. In some embodiments, the at least 3 proteins comprise at least CHLE, FETUB, and PROS. In some embodiments, the at least 3 proteins comprise any one of the triplexes presented in Table 7 or Table 8.

In another embodiment, the methods of the present disclosure include a step of detecting the level of four proteins selected from the proteins of Table 1, Table 2, Table 4, or Table 5. In another embodiment, the methods of the present disclosure include a step of detecting the level of five proteins selected from the proteins of Table 1, Table 2, Table 4, or Table 5. In another embodiment, the methods of the present disclosure include a step of detecting the level of six proteins selected from the proteins of Table 1, Table 2, Table 4, or Table 5. In another embodiment, the methods of the present disclosure include a step of detecting the level of seven proteins selected from the proteins of Table 1, Table 2, Table 4, or Table 5. In another embodiment, the methods of the present disclosure include a step of detecting the level of eight proteins selected from the proteins of Table 1, Table 2, Table 4, or Table 5.

In another embodiment, the methods of the present disclosure include a step of detecting the level of at least 3, at least 4, at least 5, at least 6, at least 7, or at least 8 proteins selected from the group consisting of FETUB, CBPN, CHLE, C9, F13B, HEMO, IC1, PROS and TRFE.

In another embodiment, the methods of the present disclosure include a step of detecting the level of least 3, at least 4, at least 5, at least 6, at least 7, or at least 8 proteins selected from the group consisting of KLKB1, APOM, ITIH4, IC1, KNG1, C9, APOL1, PGRP2, THBG, FBLN1, ITIH2, VTDB, C8A, APOA1, HPT, and TRY3.

In another embodiment, the methods of the present disclosure include a step of detecting the level of at least 3, at least 4, at least 5, at least 6, at least 7, or at least 8 proteins selected from the group consisting of AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1. In some embodiments, at least 3, at least 4, at least 5, at least 6, at least 7, or at least 8 proteins selected from the group consisting of AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1 are used to longitudinally monitor a pregnant subject's risk of spontaneous preterm birth. In some embodiments a first sample is taken between 8-14 weeks gestation (e.g. 10-12 weeks) and second sample is taken between 18-24 weeks gestation (e.g. 22-24 weeks). If upon assessment, it is determined that after the second measurement the subject is no longer at risk of spontaneous preterm birth, the management of the remainder of the pregnancy can be adjusted accordingly by a medical professional. Likewise, if upon assessment, it is determined after the second measurement the subject continues to be at risk of spontaneous preterm birth, or is at a greater risk of spontaneous preterm birth than previously determined, the management of the remainder of the pregnancy can be adjusted accordingly by a medical professional.

In another embodiment, the methods of the present disclosure include a step of detecting the level of least 3, at least 4, or at least 5 proteins selected from the group consisting of A1AG1, A2MG, CHLE, IC1, KLKB1, and TRFE.

In another embodiment, the methods of the present disclosure include a step of detecting the level of least 3, at least 4, at least 5, at least 6, at least 7, or at least 8 proteins selected from the group consisting of AACT, A1AG1, A2MG, CBPN, CHLE, C9, F13B, HEMO, IC1, KLKB1, LCAT, PGRP2, PROS, TRFE, A2AP, A2GL, APOL1, APOM, C6, CPN2, FBLN1, ITIH4, KAIN, KNG1, MBL2, SEPP1, THBG, TRY3, AMBP, APOA1, CDSL, C8A, F13A, HPT, ITIH1, and ITIH2.

In another embodiment, the methods of the present disclosure include a step of detecting the level of at least 3, at least 4, at least 5, at least 6, at least 7, or at least 8 proteins selected from the group consisting of AACT, A1AG1, A2MG, CBPN, CHLE, C9, F13B, HEMO, IC1, KLKB1, LCAT, PGRP2, PROS, and TRFE.

In another embodiment, the methods of the present disclosure include a step of detecting the level of least 3, at least 4, at least 5, at least 6, at least 7, or at least 8 proteins selected from the group consisting of A2AP, A2GL, APOL1, APOM, C6, CPN2, FBLN1, ITIH4, KAIN, KNG1, MBL2, SEPP1, THBG, and TRY3.

In another embodiment, the methods of the present disclosure include a step of detecting the level of least 3, at least 4, at least 5, at least 6, at least 7, or at least 8 proteins selected from the group consisting of AMBP, APOA1, CDSL, C8A, F13A, HPT, ITIH1, and ITIH2.

Provided herein are panels of microparticle-associated proteins indicative of an increased risk of spontaneous preterm birth. In some embodiments, the panel of microparticle-associated proteins indicative of an increased risk of spontaneous preterm birth comprises at least 3, at least 4, at least 5, at least 6, at least 7, or at least 8 proteins selected from the proteins of Table 1 or Table 2. In some embodiments, the panel of microparticle-associated proteins comprises at least 3, at least 4, at least 5, at least 6, at least 7, or at least 8 proteins selected from the proteins of Table 4. In some embodiments, the panel comprises at least 3, at least 4, at least 5, at least 6, at least 7, or at least 8 proteins selected from the proteins of Table 5. In some embodiments, the panel comprises at least 3 proteins selected from the triplexes of Table 7. In some embodiments, the panel comprises at least 3 proteins selected from the triplexes of Table 8. In some embodiments, the panel comprises at least 3, at least 4, at least 5, at least 6, at least 7, or at least 8 proteins selected from the group consisting of FETUB, CBPN, CHLE, C9, F13B, HEMO, IC1, PROS and TRFE. In some embodiments, the panel comprises at least 3, at least 4, at least 5, at least 6, at least 7, or at least 8 proteins selected from the group consisting of KLKB1, APOM, ITIH4, IC1, KNG1, C9, APOL1, PGRP2, THBG, FBLN1, ITIH2, VTDB, C8A, APOA1, HPT, and TRY3. In some embodiments, the panel comprises at least 3, at least 4, at least 5, at least 6, at least 7, or at least 8 proteins selected from the group consisting of AACT, KLKB1, APOM, ITIH4, IC1, KNG1, C9, F13B, APOL1, LCAT, PGRP2, FBLN1, ITIH2, CDSL, CBPN, VTDB, AMBP, C8A, ITIH1, TTHY, and APOA1. In some embodiments, the panel comprises at least 3, at least 4, at least 5 proteins selected from the group consisting of A1AG1, A2MG, CHLE, IC1, KLKB1, and TRFE. In some embodiments, the panel comprises at least 3 proteins selected from the group consisting of F13A, IC1, PGRP2, and THBG. In some embodiments, the panel comprises at least 3, at least 4, at least 5, at least 6, at least 7, or at least 8 proteins selected from the group consisting of AACT, A1AG1, A2MG, CBPN, CHLE, C9, F13B, HEMO, IC1, KLKB1, LCAT, PGRP2, PROS, TRFE, A2AP, A2GL, APOL1, APOM, C6, CPN2, FBLN1, ITIH4, KAIN, KNG1, MBL2, SEPP1, THBG, TRY3, AMBP, APOA1, CDSL, C8A, F13A, HPT, ITIH1, and ITIH2. In some embodiments, the panel comprises at least 3, at least 4, at least 5, at least 6, at least 7, or at least 8 proteins selected from the group consisting of AACT, A1AG1, A2MG, CBPN, CHLE, C9, F13B, HEMO, IC1, KLKB1, LCAT, PGRP2, PROS, and TRFE. In some embodiments, the panel comprises at least 3, at least 4, at least 5, at least 6, at least 7, or at least 8 proteins selected from the group consisting of A2AP, A2GL, APOL1, APOM, C6, CPN2, FBLN1, ITIH4, KAIN, KNG1, MBL2, SEPP1, THBG, and TRY3. In some embodiments, the panel comprises at least 3, at least 4, at least 5, at least 6, or at least 7 proteins selected from the group consisting of AMBP, APOA1, CDSL, C8A, F13A, HPT, ITIH1, and ITIH2. In some embodiments, the panel comprises at least HEMO, KLKB1, and TRFE. In some embodiments, the panel comprises at least A2MG, HEMO, and MBL2. In some embodiments, the panel comprises at least KLKB1, IC1, and TRFE. In some embodiments, the panel comprises at least F13A, IC1, PGRP2, and THBG. In some embodiments, the panel comprises at least IC1, PGRP2, and THBG. In some embodiments, the panel comprises at least CHLE, FETUB, and PROS.

In some embodiments, a first panel (e.g. a first trimester panel, a 8-12 week panel, or a 10-12 week panel) of microparticle-associated proteins indicative of an increased risk of spontaneous preterm birth is provided. In some embodiments, a second panel (e.g. a second trimester panel, a 18-24 week panel, or a 22-24 week panel) of microparticle-associated proteins indicative of an increased risk of spontaneous preterm birth is provided. In some embodiments, a pregnant subject is assessed for risk during the first trimester, between 8-12 weeks gestation or between 10-12 weeks gestation, and then again during the second trimester, 18-24 weeks gestation, or 22-24 weeks gestation. In such embodiments, the useful panel may comprise at least 3, at least 4, at least 5, at least 6, at least 7, or at least 8 proteins from group consisting of AACT, KLKB1, APOM, ITIH4, IC1, KNG1, C9, F13B, APOL1, LCAT, PGRP2, FBLN1, ITIH2, CDSL, CBPN, VTDB, AMBP, CBA, ITIH1, TTHY, and APOA1. In some embodiments, the first trimester panel In some embodiments of the panels presented herein, the panel of microparticle-associated proteins indicative of an increased risk of spontaneous preterm birth comprises no more than 30, no more than 25, no more than 20, no more than 15, no more than 10, no more than 9, no more than 8, no more than 7, no more than 6, or no more than 5 microparticle-associated proteins. In an exemplary embodiment, the panel of microparticle-associated proteins indicative of an increased risk of spontaneous preterm birth comprises no more than 5 proteins. In another exemplary embodiment, the panel of microparticle-associated proteins indicative of an increased risk of spontaneous preterm birth comprises no more than 6 proteins. In another exemplary embodiment, the panel of microparticle-associated proteins indicative of an increased risk of spontaneous preterm birth comprises no more than 7 proteins. In another exemplary embodiment, the panel of microparticle-associated proteins indicative of an increased risk of spontaneous preterm birth comprises no more than 8 proteins.

In some embodiments, provided herein is a method comprising: preparing a microparticle-enriched fraction from a blood sample from the pregnant subject; and determining a quantitative measure of any one of the panels of microparticle-associated proteins provided herein.

Pregnant Subjects

The tools and methods provided herein can be used to assess the risk of SPTB in a pregnant subject, wherein the subject can be any mammal, of any species. In some embodiments of the present disclosure, the pregnant subject is a human female. In some embodiments, the pregnant human subject is in the first trimester (e.g., weeks 1-12 of gestation), second trimester (e.g., weeks 13-28 of gestation) or third trimester of pregnancy (e.g., weeks 29-37 of gestation). In some embodiments, the pregnant human subject is in early pregnancy (e.g., from 8, 9, 10, 11, 12, 13, 14, 15, 16, 17, 18, 19 or 20, but earlier than 21 weeks of gestation; from 20, 19, 18, 17, 16, 15, 14, 13, 12, 11, 10 or 9, but later than 8 weeks of gestation). In some embodiments, the pregnant human subject is in mid-pregnancy (e.g., from 21, 22, 23, 24, 25, 26, 27, 28, 29 or 30, but earlier than 31 weeks of gestation; from 30, 29, 28, 27, 26, 25, 24, 23, 22 or 21, but later than 20 weeks of gestation). In some embodiments, the pregnant human subject is in late pregnancy (e.g., from 31, 32, 33, 34, 35, 36 or 37, but earlier than 38 weeks of gestation; from 37, 36, 35, 34, 33, 32 or 31, but later than 30 weeks of gestation). In some embodiments, the pregnant human subject is in less than 17 weeks, less than 16 weeks, less than 15 weeks, less than 14 weeks or less than 13 weeks of gestation; from 20, 19, 18, 17, 16, 15, 14, 13, 12, 11, 10 or 9, but later than 8 weeks of gestation). In some embodiments, the pregnant human subject is in about 8-12 weeks of gestation. In some embodiments, the pregnant human subject is in about 18-24 weeks of gestation. In an exemplary embodiment, the pregnant human subject is at 10-12 weeks of gestation. In some embodiments, the pregnant human subject is in about 22-24 weeks of gestation. The stage of pregnancy can be calculated from the first day of the last normal menstrual period of the pregnant subject.

In some embodiments, the pregnant human subject is primagravida. In other embodiments, the pregnant subject multigravida. In some embodiments, the pregnant subject may have had at least one prior spontaneous preterm birth (e.g., birth prior to week 38 of gestation). In some embodiments, the pregnant human subject is asymptomatic. In some embodiments, the subject may have a risk factor of PTB such as a history of pre-gestational hypertension, diabetes mellitus, kidney disease, known thrombophilias and/or other significant preexisting medical condition (e.g., short cervical length).

Samples

A sample for use in the methods of the present disclosure is a biological sample obtained from a pregnant subject. In preferred embodiments, the sample is collected during a stage of pregnancy described in the preceding section. In some embodiments, the sample is a blood, saliva, tears, sweat, nasal secretions, urine, amniotic fluid or cervicovaginal fluid sample. In some embodiments, the sample is a blood sample, which in preferred embodiments is serum or plasma. In some embodiments, the sample has been stored frozen (e.g., −20° C. or −80° C.).

Methods for Assessing Risk of Spontaneous Preterm Birth

The phrase "increased risk of spontaneous preterm birth" as used herein indicates that a pregnant subject has a greater likelihood of having a spontaneous preterm birth (before 38 weeks gestation) when one or more preterm birth markers are detected, when a particular panel of microparticle-associated proteins indicative of an increased risk of spontaneous preterm birth are detected, and/or when one or more term birth markers are not detected. In some embodiments, assessing risk of spontaneous preterm birth involves assigning a probability on the risk of preterm birth. In some embodiments, assessing risk of spontaneous preterm birth involves stratifying a pregnant subject as being at high risk, moderate risk, or low risk of spontaneous preterm birth. In some embodiments, assessing risk of spontaneous preterm birth involves determining whether a pregnant subject's risk is increased or decreased, as compared to the population as a whole, or the population in a particular demographic (age, weight, medical history, geography, and/or other factors). In some embodiments, assessing risk of spontaneous preterm birth involves assigning a percentage risk of spontaneous preterm birth.

In some embodiments, the methods provided herein indicate that a pregnant subject has a greater likelihood of having a spontaneous preterm birth between 37 and 38 weeks gestation. In some embodiments, the methods provided herein indicate that a pregnant subject has a greater likelihood of having a spontaneous preterm birth before 37 weeks gestation. In some embodiments, the methods provided herein indicate that a pregnant subject has a greater likelihood of having a spontaneous preterm birth before 36 weeks gestation. In some embodiments, the methods provided herein indicate that a pregnant subject has a greater likelihood of having a spontaneous preterm birth before 35 weeks gestation. In some embodiments, the methods provided herein indicate that a pregnant subject has a greater likelihood of having a spontaneous preterm birth before 34 weeks gestation. In some embodiments, the methods provided herein indicate that a pregnant subject has a greater likelihood of having a spontaneous preterm birth before 33 weeks gestation. In some embodiments, the methods provided herein indicate that a pregnant subject has a greater likelihood of having a spontaneous preterm birth before 32 weeks gestation.

Numerically an increased risk is associated with a hazard ratio of over 1.0, preferably over 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 for preterm birth.

In some embodiments, detecting the level (e.g., including detecting the presence) of one or both of spontaneous preterm birth biomarkers and term birth biomarkers is done using a liquid chromatography/mass spectrometry (LC/MS)-based proteomic analysis. In an exemplary embodiment the method involves subjecting a sample to size exclusion chromatography and collecting the high molecular weight fraction to obtain a microparticle-enriched sample. The microparticle-enriched sample is then extracted before digestion with a proteolytic enzyme such as trypsin to obtain a digested sample comprising a plurality of peptides. The digested sample is then subjected to a peptide purification/concentration step before liquid chromatography and mass spectrometry to obtain a proteomic profile of the sample. In some embodiments, the purification/concentration step comprises reverse phase chromatography (e.g., ZIPTIP pipette tip with 0.2 μL C18 resin, from Millipore Corporation, Billerica, Mass.).

In some embodiments, detecting the level (e.g., including detecting the presence) of one or both of spontaneous preterm birth biomarkers and term birth biomarkers is done using an antibody-based method. Suitable antibody-based methods include but are not limited to enzyme linked immunosorbent assay (ELISA), chemiluminescent assay, Western blot, and antibody microarray.

Methods of assessing risk of spontaneous preterm birth can involve classifying a subject as at increased risk of spontaneous preterm birth based on information including at least a quantitative measure of at least one biomarker of this disclosure. Classifying can employ a classification algorithm or model. Many types of classification algorithms are suitable for this purpose, including linear and non-linear models, e.g., processes such as CART—classification and regression trees), artificial neural networks such as back propagation networks, discriminant analyses (e.g., Bayesian classifier or Fischer analysis), logistic classifiers, and support vector classifiers (e.g., support vector machines). Certain classifiers, such as cut-offs, can be executed by human inspection. Other classifiers, such as multivariate classifiers, can require a computer to execute the classification algorithm.

Classification algorithms can be generated by mathematical analysis, including by machine learning algorithms that perform analysis of datasets of biomarker measurements derived from subjects classed into one or another group. Many machine learning algorithms are known in the art, including those that generate the types of classification algorithms above.

Diagnostic tests are characterized by sensitivity (percentage classified as positive that are true positives) and specificity (percentage classified as negative that are true negatives). The relative sensitivity and specificity of a diagnostic test can involve a trade-off—higher sensitivity can mean lower specificity, while higher specificity can mean lower sensitivity. These relative values can be displayed on a receiver operating characteristic (ROC) curve. The diagnostic power of a set of variables, such as biomarkers, is reflected by the area under the curve (AUC) of an ROC curve.

In some embodiments, the classifiers of this disclosure have a sensitivity of at least 85%, at least 90%, at least 95%, at least 98%, or at least 99%. Classifiers of this disclosure have an AUC of at least 0.6, at least 0.7, at least 0.8, at least 0.9 or at least 0.95.

Methods for Reducing Risk of Spontaneous Preterm Birth

In one embodiment, if a pregnant subject is determined to be at increased risk of spontaneous preterm birth, the appropriate treatment plans can be employed. By way of example, a surgical intervention such as cervical cerclage and progesterone supplementation have been shown to be effective in preventing preterm birth (Committee on Practice Bulletins, Obstetrics & Gynecology, 120:964-973, 2012). In some embodiments, other measures are taken by health care professionals, such as switching to an at-risk protocol such as increased office visits and/or tracking the patient to a physician specially trained to deal with high risk patients. In some embodiments, if a pregnant subject is determined to be at increased risk of spontaneous preterm birth, steps can be taken such that the pregnant subject will have access to NICU facilities and plans for access to such facilities for rural patients. Additionally, the pregnant subject and family members can have better knowledge of acute-phase symptomatic interventions such as fetal fibronectin testing (diagnostic) and corticosteroids (e.g. for baby lung development) and mag sulfate (e.g. for baby neuroprotective purposes). Additionally, the pregnant subject can be monitored such as better adherence to dietary, smoking cessation, and other recommendations from the physician are followed.

In one embodiment, the pregnant subject is prescribed progesterone supplementation. Currently progesterone supplementation for the prevention of recurrent spontaneous preterm birth is offered to: females with a singleton pregnancy and a prior spontaneous preterm birth; and females with no history of spontaneous preterm birth who have an incidentally detected very short cervix (<15 mm). The present disclosure provides tools to identify additional pregnant subjects that may benefit from progesterone supplementation. These subjects include the following: pregnant females who are primigravidas without a history of risk and without an incidentally detected very short cervix; and pregnant females who are multigravidas but who did not previously have a spontaneous preterm birth.

Pregnant subjects determined to be at increased risk for preterm birth are recommended to receive or are administered progesterone until 36 weeks of gestation (e.g., upon identification or between 16 weeks, 0 days and 20 weeks, 6 days gestation until 36 weeks gestation). In some embodiments, progesterone supplementation comprises 250 mg weekly intramuscular injections. In an exemplary embodiment, the weekly progesterone supplementation comprises administration of hydroxyprogesterone caproate by injection. In other embodiments, progesterone supplementation comprises vaginal progesterone in doses between 50 and 300 mg daily, between 75 and 200 mg daily or between 90 and 110 mg daily.

In another embodiment, in females with a singleton pregnancy determined to be at increased risk for preterm birth and who have had a documented prior spontaneous preterm birth at less than 34 weeks of gestation and short cervical length (less than 25 mm) before 24 weeks of gestation, are recommended to receive or are given a cervical cerclage (also known as tracheloplasty or cervical stitch). In some embodiments, the cervical cerclage is a McDonald cerclage, while in other embodiments it is a Shirodkar cerclage or an abdominal cerclage.

Accordingly, provided herein is one method of decreasing risk of spontaneous preterm birth for a pregnant subject and/or reducing neonatal complications of spontaneous preterm birth, the method comprising: assessing risk of spontaneous preterm birth for a pregnant subject according to any of the methods provided herein; and administering a therapeutic agent, prescribing a revised care management protocol, carrying out fetal fibronectin testing, administering corticosteroids, administering mag sulfate, or increasing the monitoring and surveillance of the subject in an amount effective to decrease the risk of spontaneous preterm birth and/or reduce neonatal complications of spontaneous preterm birth. In some embodiments, the therapeutic agent is selected from the group consisting of a hormone and a corticosteroid. In some embodiments, the therapeutic agent comprises vaginal progesterone or parenteral 17-alpha-hydroxyprogesterone caproate.

Kits

In another embodiment, a kit of reagents capable of one or both of spontaneous preterm birth biomarkers and term birth biomarkers in a sample is provided. Reagents capable of detecting protein biomarkers include but are not limited to antibodies. Antibodies capable of detecting protein biomarkers are also typically directly or indirectly linked to a molecule such as a fluorophore or an enzyme, which can catalyze a detectable reaction to indicate the binding of the reagents to their respective targets.

In some embodiments, the kits further comprise sample processing materials comprising a high molecular gel filtration composition (e.g., agarose such as SEPHAROSE) in a low volume (e.g., 1 ml) vertical column for rapid preparation of a microparticle-enriched sample from plasma. For instance, the microparticle-enriched sample can be prepared at the point of care before freezing and shipping to an analytical laboratory for further processing, for example by size exclusion chromatography.

In some embodiments, the kits further comprise instructions for assessing risk of spontaneous preterm birth. As used herein, the term "instructions" refers to directions for using the reagents contained in the kit for detecting the presence (including determining the expression level) of a protein(s) of interest in a sample from a subject. The proteins of interest may comprise one or both of spontaneous preterm birth biomarkers and term birth biomarkers. In some embodiments, the instructions further comprise the statement of intended use required by the U.S. Food and Drug Administration (FDA) in labeling in vitro diagnostic products. The FDA classifies in vitro diagnostics as medical devices and required that they be approved through the 510(k) procedure. Information required in an application under 510(k) includes: 1) The in vitro diagnostic product name, including the trade or proprietary name, the common or usual name, and the classification name of the device; 2) The intended use of the product; 3) The establishment registration number, if applicable, of the owner or operator submitting the 510(k) submission; the class in which the in vitro diagnostic product was placed under section 513 of the FD&C Act, if known, its appropriate panel, or, if the owner or operator determines that the device has not been classified under such section, a statement of that determination and the basis for the determination that the in vitro diagnostic product is not so classified; 4) Proposed labels, labeling and advertisements sufficient to describe the in vitro diagnostic product, its intended use, and directions for use, including photographs or engineering drawings, where applicable; 5) A statement indicating that the device is similar to and/or different from other in vitro diagnostic products of comparable type in commercial distribution in the U.S., accompanied by data to support the statement; 6) A 510(k) summary of the safety and effectiveness data upon which the substantial equivalence determination is based; or a statement that the 510(k) safety and effectiveness information supporting the FDA finding of substantial equivalence will be made available to any person within 30 days of a written request; 7) A statement that the submitter believes, to the best of their knowledge, that all data and information submitted in the premarket notification are truthful and accurate and that no material fact has been omitted; and 8) Any additional information regarding the in vitro diagnostic product requested that is necessary for the FDA to make a substantial equivalence determination.

The invention will be more fully understood by reference to the following examples. They should not, however, be construed as limiting the scope of the invention. It is understood that the examples and embodiments described herein are for illustrative purposes only.

EXAMPLES

Abbreviations: AUC (area under curve); CI (confidence interval); CMP (circulating microparticles); DDN (Differential Dependency Network); FDR (false discovery rate); LC (liquid chromatography); LMP (last menstrual period); MRM (multiple reaction monitoring); MS (mass spectrometry); ROC (receiver operating characteristic); SEC (size exclusion chromatography); SPTB (spontaneous preterm birth); and TERM (full term birth).

Example 1: Identification of SPTB Biomarkers in Samples Obtained Between 10-12 Weeks Gestation This example describes a study utilizing plasma samples obtained between 10-12 weeks gestation as part of a prospectively collected birth cohort. Singleton cases of SPTB prior to 34 weeks were matched by maternal age, race and gestational age of sampling to uncomplicated term deliveries after 37 weeks. Circulating microparticles (CMPs) from first trimester samples were isolated and subsequently analyzed by multiple reaction monitoring mass spectrometery (MRM-MS) to identify protein biomarkers. SPTB <34 weeks was assessed given the increased neonatal morbidity in that gestational age range.

Materials and Methods
Clinical Data and Specimen Collection.

Clinical data and maternal K2-EDTA plasma samples (10-12 weeks gestation) were obtained and stored at −80° C. at Brigham and Women's Hospital (BWH), Boston, Mass. between 2009-2014 as part of the prospectively collected LIFECODES birth cohort (McElrath et al., Am J Obstet Gynecol, 207:407-414, 2012). Eligibility criteria included patients who were >18 yrs of age, initiated their prenatal care at <15 weeks of gestation and planned on delivering at the BWH. Exclusion criteria included preexisting medical disorders and fetal anomalies. Gestational age of pregnancy was confirmed by ultrasound scanning ≤12 weeks gestation. If consistent with last menstrual period (LMP) dating, the LMP was used to determine the due date. If not consistent, then the due date was set by the earliest available ultrasound. Full-term birth was defined as after 37 weeks of gestation, and preterm birth for the purposes of this investigation was defined as SPTB prior to 34 weeks. All cases were independently reviewed and validated by two board certified maternal fetal medicine physicians. When disagreement in pregnancy outcome or characteristic arose, the case was re-reviewed and a consensus conference held to determine the final characterization. Twenty-five singleton cases of SPTB prior to 34 weeks were matched to two control term deliveries by maternal age, race, and gestational age of sampling (plus or minus two weeks).

CMP Enrichment.

Plasma samples were shipped on dry ice to the David H Murdock Research Institute (DHMRI, Kannapolis, N.C.) and randomized to blind laboratory personnel performing sample processing and testing to case/control status. CMPs were enriched by size exclusion chromatography (SEC) and isocratically eluted using water (RNAse free, DNAse free, distilled water). Briefly, PD-10 columns (GE Healthcare Life Sciences) were packed with 10 mL of 2% agarose bead standard (pore size 50-150 um) from ABT (Miami, Fla.), washed and stored at 4° C. for a minimum of 24 hrs and no longer than three days prior to use. On the day of use columns were again washed and 1 mL of thawed neat plasma sample was applied to the column. That is, the plasma samples were not filtered, diluted or treated prior to SEC.

The circulating microparticles were captured in the column void volume, partially resolved from the high abundant protein peak (Ezrin et al., Am J Perinatol, 32:605-614, 2015). The samples were processed in batches of 15 to 20 across four days to minimize variability between processing individual samples. One aliquot of the pooled CMP column fraction from each clinical specimen, containing 200 µg of total protein (determined by BCA) was transferred to a 2 mL microcentrifuge tube (VWR) and shipped on dry ice to Biognosys (Zurich, Switzerland) for proteomic analysis.

Liquid Chromatography-Mass Spectrometry.

Quantitative proteomic liquid chromatography-mass spectrometry (LC-MS) analysis was performed by Biognosys AG. Briefly, for each sample 20 µg of total protein was lyophilized and then denatured with 8M urea, reduced using dithiothreitol, alkylated with iodoacetamide, and digested overnight with trypsin (Promega). Resulting sample peptides were dried using a SpeedVac system and re-dissolved in 45 µL of Biognosys LC solvent and mixed with Biognosys PlasmaDive (extended version 2.0) stable isotope-labeled reference peptide mix containing Biognosys iRT kit.

Then 1 µg of total protein was injected into an in-house packed C18 column (75 µm inner diameter and 10 cm column length, New Objective); column material was Magic AQ, 3 µm particle size, 200 Å pore size from Michrom) on a Thermo Scientific Easy nLC nano-liquid chromatography system. LC-MRM assays were measured on a Thermo Scientific TSQ Vantage triple quadrupole mass spectrometer equipped with a standard nano-electrospray source. The LC gradient for LC-MRM was 5-35% solvent B (97% acetonitrile in water with 0.1% FA) in 30 minutes followed by 35-100% solvent B in 2 minutes and 100% solvent B for 8 minutes (total gradient length was 40 minutes). For quantification of the peptides across samples, the TSQ Vantage was operated in scheduled MRM mode with an acquisition window length of 3.25 minutes. The LC eluent was electrosprayed at 1.9 kV and Q1 was operated at unit resolution (0.7 Da). Signal processing and data analysis was carried out using SpectroDive™ Biognosys' software for multiplexed MRM data analysis based on mProphet (Reiter et al., Nature Methods, 8:430-435, 2011). A Q-value filter of 1% was applied. Protein concentration was determined based on the normalized 1 µg of protein injected into the LC/MS.

Statistical Analysis.

To select informative analytes that differentiate SPTB from term deliveries, the processed protein quantitation data were first subjected to univariate receiver-operating characteristic (ROC) curve analysis (Fawcett, Pattern Recognition Letters, 27:861-874, 2006; and Robin et al., BMC Bioinformatics, 19:12:77, 2011). Bootstrap resampling against nulls from sample label permutation was used to control the false-discovery rate (FDR) (Carpenter and Bithell, Statistics in Medicine, 19:1141-1164, 2000; and Xie et al., Bioinformatics, 21:4280-4288, 2005). Briefly, for each protein, a ROC analysis was repeated on bootstrap samples from the original data, the mean and standard deviation (SD) of the area-under-curve (AUC) was estimated. The bootstrap procedure was then applied on the same data again but with sample SPTB status labels randomly permutated. The permutation analysis provided the null results in order to control the FDR and adjust for multiple comparison during the selection of candidate protein biomarkers. The Differential Dependency Network (DDN) bioinformatic tool was then applied in order to extract SPTB phenotype-dependent high-order co-expression patterns among the proteins (Tian et al., Bioinformatics, 32:287-289, 2015). An additional bioinformatic tool, BiNGO, was used to identify gene ontology categories that were overrepresented in the DDN subnetworks in order to explore functional links between the observed proteomic dis-regulations and SPTB (Maere et al., Bioinformatics, 21:3448-3449, 2005). In order to assess the complementary values among the selected proteins and the range of their potential clinically relevant performance, multivariate linear models were derived and evaluated using bootstrap resampling.

Results

The demographic and clinical characteristics of the sample set are presented in Table 3. Maternal age, race, body mass index (BMI), use of public insurance, smoking during pregnancy, and gestational age at enrollment were similar in both groups. Maternal educational levels were higher in the controls and a greater proportion of the SPTB cases tended to be primiparous.

TABLE 3

Baseline characteristics of SPTB vs. term control pregnancies

| Characteristic | SPTB (N = 25) N (%) or Mean (SD) | Controls (N = 50) N (%) or Mean (SD) | p-value[a] |
|---|---|---|---|
| Maternal Age (yrs.) | 32.8 (7.3) | 31.6 (5.8) | 0.44 |
| Race | | | 0.10 |
| Caucasian | 8 (32.0%) | 23 (46.0%) | |
| African-American | 3 (12.0%) | 5 (10.0%) | |
| Hispanic | 8 (32.0%) | 18 (36.0%) | |
| Asian | 3 (12.0%) | 2 (4.0%) | |
| Other | 3 (12.0%) | 2 (4.0%) | |

TABLE 3-continued

Baseline characteristics of SPTB vs. term control pregnancies

| Characteristic | SPTB (N = 25) N (%) or Mean (SD) | Controls (N = 50) N (%) or Mean (SD) | p-value[a] |
|---|---|---|---|
| Maternal BMI (kg/m$^2$) | 29.3 (6.9) | 27.3 (7.4) | 0.17 |
| Maternal Education | | | 0.004 |
| <High School | 3 (12.0%) | 0 (0.0%) | |
| High School/Equivalent | 1 (4.0%) | 0 (0.0%) | |
| >High School | 21 (84.0%) | 50 (100.0%) | |
| On Public Insurance | 10 (40.0%) | 14 (28.0%) | 0.31 |
| Primiparous | 14 (56.0%) | 15 (30.0%) | 0.04 |
| Smoked During Pregnancy | 4 (8.0%) | 1 (4.0%) | 0.66 |
| Enrollment Gestational age | 11.7 (3.0) | 11.6 (3.0) | 0.99 |

[a]P-values calculated with Wilcoxon Rank Sum test, Chi Square test, Fisher Exact test or ANOVA where appropriate The 132 proteins evaluated via targeted MRM were individually assessed for ability to differentiate SPTB from term deliveries. By requiring that the mean bootstrap AUCs for each candidate protein be significantly greater than the null (>mean+SD of mean bootstrap AUCs estimated with label permutation) and excluding proteins with large bootstrap AUCs variances, 62 of the 132 proteins demonstrated robust power for the detection of SPTB (lower right quadrant of FIG. 1). In contrast, using the same criteria with sample label permutation, only 12 proteins would have been selected. The estimated FDR for protein selection was therefore <20% (12/62). These 62 proteins were considered candidates for further multivariate analysis. Table 4 provides performance values for proteins that were downregulated (−) in SPTB cases versus TERM controls, or were unregulated (+) in SPTB cases vs TERM controls. The p value, AUC, and Specificity when Sensitivity is fixed at 65% is shown for biomarkers ranked by AUC from highest to lowest.

TABLE 4

Performance of Single Analytes With Dysregulation

| Names | Direction | AUC | p value | Spec @ Sens 65% |
|---|---|---|---|---|
| AACT | − | 0.715 | 0.003 | 0.740 |
| KLKB1 | − | 0.678 | 0.013 | 0.680 |
| APOM | − | 0.674 | 0.015 | 0.680 |
| ITIH4 | − | 0.662 | 0.024 | 0.660 |
| IC1 | − | 0.651 | 0.034 | 0.460 |
| KNG1 | − | 0.650 | 0.035 | 0.500 |
| TRY3 | − | 0.644 | 0.048 | 0.625 |
| C9 | − | 0.639 | 0.051 | 0.500 |
| F13B | − | 0.635 | 0.058 | 0.580 |
| APOL1 | − | 0.634 | 0.060 | 0.520 |
| LCAT | − | 0.633 | 0.062 | 0.640 |
| PGRP2 | − | 0.631 | 0.067 | 0.600 |
| THBG | − | 0.628 | 0.072 | 0.500 |
| FBLN1 | − | 0.628 | 0.073 | 0.420 |
| ITIH2 | − | 0.628 | 0.073 | 0.540 |
| CD5L | − | 0.627 | 0.075 | 0.580 |
| CBPN | − | 0.626 | 0.077 | 0.520 |
| PROS | + | 0.624 | 0.132 | 0.548 |
| VTDB | − | 0.624 | 0.082 | 0.500 |
| AMBP | − | 0.622 | 0.087 | 0.480 |
| C8A | − | 0.622 | 0.087 | 0.580 |
| ITIH1 | − | 0.622 | 0.089 | 0.520 |
| TTHY | − | 0.619 | 0.095 | 0.480 |
| F13A | − | 0.619 | 0.097 | 0.531 |
| APOA1 | − | 0.618 | 0.100 | 0.540 |
| HPT | − | 0.618 | 0.100 | 0.540 |
| HABP2 | − | 0.615 | 0.107 | 0.520 |
| PON1 | − | 0.612 | 0.118 | 0.600 |
| SEPP1 | − | 0.611 | 0.120 | 0.460 |
| ZA2G | − | 0.610 | 0.125 | 0.540 |
| A2GL | − | 0.607 | 0.134 | 0.520 |

TABLE 4-continued

Performance of Single Analytes With Dysregulation

| Names | Direction | AUC | p value | Spec @ Sens 65% |
|---|---|---|---|---|
| A2MG | − | 0.606 | 0.139 | 0.440 |
| APOD | − | 0.605 | 0.142 | 0.560 |
| CHLE | − | 0.603 | 0.149 | 0.500 |
| CPN2 | − | 0.603 | 0.149 | 0.480 |
| CLUS | − | 0.602 | 0.152 | 0.400 |
| PLF4 | + | 0.601 | 0.194 | 0.524 |
| THRB | − | 0.597 | 0.176 | 0.420 |
| A1BG | − | 0.590 | 0.206 | 0.560 |
| TREE | + | 0.590 | 0.206 | 0.540 |
| ZPI | − | 0.585 | 0.241 | 0.420 |
| HEMO | + | 0.583 | 0.247 | 0.440 |
| ATRN | − | 0.582 | 0.249 | 0.480 |
| KAIN | − | 0.580 | 0.263 | 0.500 |
| A1AG1 | − | 0.578 | 0.273 | 0.500 |
| FIBA | − | 0.575 | 0.293 | 0.540 |
| FETUA | − | 0.573 | 0.309 | 0.420 |
| GPX3 | − | 0.571 | 0.320 | 0.531 |
| HEP2 | − | 0.571 | 0.320 | 0.420 |
| FETUB | + | 0.571 | 0.326 | 0.592 |
| C8G | − | 0.570 | 0.325 | 0.480 |
| HPTR | − | 0.570 | 0.325 | 0.400 |
| IGJ | − | 0.568 | 0.342 | 0.460 |
| MBL2 | − | 0.567 | 0.348 | 0.520 |
| C6 | − | 0.567 | 0.348 | 0.440 |
| C1R | − | 0.566 | 0.354 | 0.460 |
| MASP1 | − | 0.563 | 0.378 | 0.440 |
| SAA4 | + | 0.563 | 0.378 | 0.400 |
| FINC | − | 0.562 | 0.390 | 0.400 |
| FCN3 | − | 0.559 | 0.409 | 0.500 |
| A1AG2 | − | 0.556 | 0.435 | 0.480 |
| FA10 | − | 0.556 | 0.435 | 0.340 |
| A1AT | − | 0.554 | 0.455 | 0.400 |
| FA12 | − | 0.551 | 0.488 | 0.362 |
| APOA4 | − | 0.550 | 0.482 | 0.360 |

Individually, 25 of the 62 proteins had the lowest p values (≤0.10) and greatest AUC (≥0.618) for differentiating SPTB from term controls (Table 5).

TABLE 5

Discriminating Single Analytes

| Protein | p-value | AUC |
|---|---|---|
| AACT | 0.003 | 0.715 |
| KLKB1 | 0.013 | 0.678 |
| APOM | 0.015 | 0.674 |
| ITIH4 | 0.024 | 0.662 |
| IC1 | 0.034 | 0.651 |
| KNG1 | 0.035 | 0.650 |
| TRY3 | 0.048 | 0.644 |
| C9 | 0.051 | 0.639 |
| F13B | 0.058 | 0.635 |
| APOL1 | 0.060 | 0.634 |
| LCAT | 0.062 | 0.633 |
| PGRP2 | 0.067 | 0.631 |
| THBG | 0.072 | 0.628 |
| FBLN1 | 0.073 | 0.628 |
| ITIH2 | 0.073 | 0.628 |
| CD5L | 0.075 | 0.627 |
| CBPN | 0.077 | 0.626 |
| VTDB | 0.082 | 0.624 |
| AMBP | 0.087 | 0.622 |
| C8A | 0.087 | 0.622 |
| ITIH1 | 0.089 | 0.622 |
| TTHY | 0.095 | 0.619 |
| F13A | 0.097 | 0.619 |
| APOA1 | 0.100 | 0.618 |
| HPT | 0.100 | 0.618 |

Figure 2:
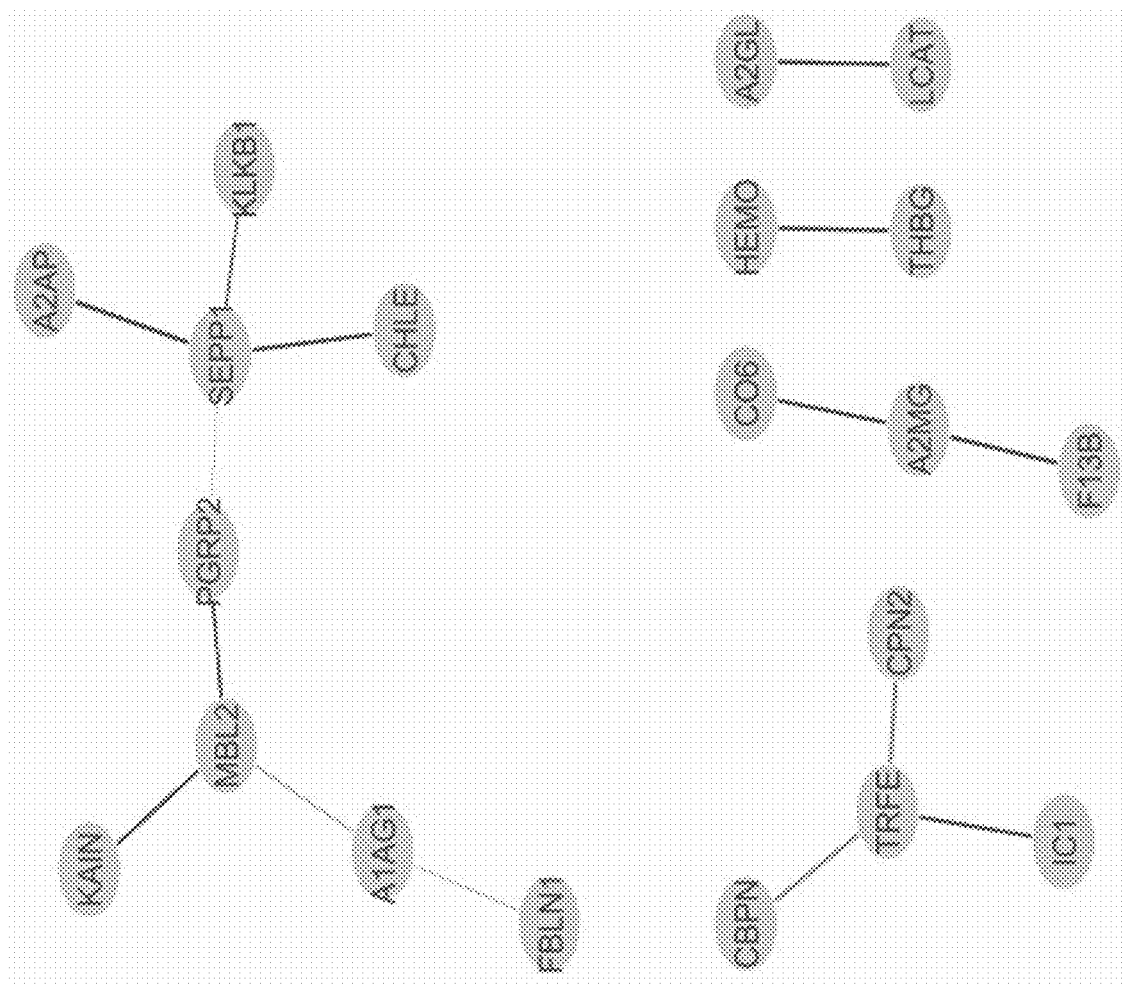
FIG. 2 illustrates a Differential Dependency Network (DDN) analysis of selected proteins identified as having co-expression patterns associated with STPB. In the plot, red lines indicate that co-expression between the pairs of proteins were observed among STPBs, while green lines indicate that co-expression between the pairs of proteins were observed among the TERM cases. The thickness of the lines is proportional to the statistical significance of the connection.

Differential dependency network analysis among the 62 selected proteins identified a number of SPTB phenotype-associated co-expression patterns (FIG. 2). A number of gene ontology categories, such as inflammation, wound healing, the coagulation cascade, and steroid metabolism were overrepresented among the DDN analysis co-expression subnetworks. Table 6 provides a listing of the top discriminating pairwise correlations (p-values <0.001-0.069). There were a total of 20 unique proteins that formed the DDN subnetworks. Several of the pairwise correlations (CBPN-TRFE, CPN2-TRFE, A1AG1-MBL2) were markers for inclusion in the TERM controls rather than the SPTB cases, indicative of protection against SPTB.

TABLE 6

Pair-Wise Connections Between Proteins

| Protein 1 | Protein 2 | Phenotype | p-value |
|---|---|---|---|
| A2AP | SEPP1 | SPTB | <0.001 |
| CBPN | TRFE | TERM | <0.001 |
| CPN2 | TRFE | TERM | <0.001 |
| HEMO | THBG | SPTB | 0.002 |
| A2MG | F13B | SPTB | 0.003 |
| IC1 | TRFE | SPTB | 0.003 |
| KAIN | MBL2 | SPTB | 0.004 |
| A2GL | LCAT | SPTB | 0.005 |
| A2MG | C6 | SPTB | 0.005 |
| CHLE | SEPP1 | SPTB | 0.009 |
| MBL2 | PGRP2 | SPTB | 0.022 |
| KLKB1 | SEPP1 | SPTB | 0.045 |
| A1AG1 | MBL2 | TERM | 0.064 |
| PGRP2 | SEPP1 | SPTB | 0.066 |
| A1AG1 | FBLN1 | SPTB | 0.069 |

Based on the available sample size, and in order to avoid overtraining, only linear models were evaluated to assess the clinically relevant performance and the variables were limited to all possible combinations of two or three proteins out of the 20 proteins in Table 6 (1330 models). Each model was derived and evaluated using 200 bootstrap resampled data in order to estimate the median (90% CI) and specificity for ROC AUCs with a fixed sensitivity of 80%. The top 20 models in terms of the lower-bound of 90% CI of AUCs and specificities are listed in Table 7 and Table 8, respectively. Given limitations imposed by the sample size, the model could not be tested on an independent sample set. To compensate for this the CIs for the panel's performances in the training dataset were estimated through iterative bootstrap analysis. Table 7 shows triplexes from that which, when sensitivity is set at 80%, have the best the area under the curve (AUC). Table 8 shows triplexes from study D which, when sensitivity is set at 80%, have the best specificity.

TABLE 7

Top 20 Models Based on the Lower Bound of 90% CI of AUC from ROC analysis (SPTB vs. term controls)

| Panel | Specificity at 80% sensitivity Median (90% CI) | AUC Median (90% CI) |
|---|---|---|
| A2MG HEMO MBL2 | 0.830 (0.654, 0.935) | 0.892 (0.829, 0.949) |
| HEMO IC1 KLKB1 | 0.842 (0.666, 0.927) | 0.892 (0.824, 0.942) |
| A2MG HEMO KLKB1 | 0.812 (0.634, 0.933) | 0.879 (0.819, 0.945) |
| A1AG1 A2MG HEMO | 0.824 (0.666, 0.940) | 0.887 (0.815, 0.943) |
| A1AG1 A2MG C6 | 0.800 (0.630, 0.922) | 0.876 (0.814, 0.932) |
| F13B HEMO KLKB1 | 0.808 (0.643, 0.907) | 0.878 (0.810, 0.931) |
| IC1 KLKB1 TRFE | 0.837 (0.680, 0.939) | 0.882 (0.808, 0.943) |
| HEMO IC1 LCAT | 0.825 (0.653, 0.932) | 0.879 (0.808, 0.938) |
| KLKB1 LCAT TRFE | 0.830 (0.683, 0.935) | 0.870 (0.807, 0.943) |
| A1AG1 KLKB1 TRFE | 0.804 (0.630, 0.919) | 0.876 (0.806, 0.935) |
| A1AG1 HEMO KLKB1 | 0.808 (0.659, 0.918) | 0.872 (0.805, 0.931) |

TABLE 7-continued

Top 20 Models Based on the Lower Bound of 90% CI of AUC from ROC analysis (SPTB vs. term controls)

| Panel | Specificity at 80% sensitivity Median (90% CI) | AUC Median (90% CI) |
|---|---|---|
| A2MG KLKB1 TRFE | 0.811 (0.632, 0.932) | 0.878 (0.804, 0.937) |
| CPN2 HEMO KLKB1 | 0.804 (0.630, 0.922) | 0.871 (0.803, 0.936) |
| A2GL A2MG HEMO | 0.796 (0.543, 0.923) | 0.872 (0.803, 0.933) |
| HEMO KLKB1 PGRP2 | 0.800 (0.637, 0.939) | 0.873 (0.801, 0.932) |
| HEMO KLKB1 LCAT | 0.816 (0.674, 0.940) | 0.874 (0.801, 0.944) |
| A2AP KLKB1 TRFE | 0.821 (0.666, 0.927) | 0.865 (0.800, 0.947) |
| KLKB1 LCAT PGRP2 | 0.808 (0.667, 0.918) | 0.872 (0.798, 0.939) |
| A2MG LCAT TRFE | 0.823 (0.619, 0.928) | 0.871 (0.798, 0.934) |
| A1AG1 HEMO IC1 | 0.802 (0.500, 0.898) | 0.861 (0.797, 0.921) |

TABLE 8

Top 20 Models Based on the Lower Bound of 90% CI of Specificity at Fixed 80% Sensitivity (SPTB vs. term controls)

| Panel | Specificity at 80% sensitivity Median (90% CI) | AUC Median (90% CI) |
|---|---|---|
| KLKB1 LCAT TRFE | 0.830 (0.683, 0.935) | 0.870 (0.807, 0.943) |
| IC1 KLKB1 TRFE | 0.837 (0.680, 0.939) | 0.882 (0.808, 0.943) |
| HEMO KLKB1 LCAT | 0.816 (0.674, 0.940) | 0.874 (0.801, 0.944) |
| A2GL KLKB1 TRFE | 0.808 (0.674, 0.920) | 0.865 (0.797, 0.925) |
| KLKB1 LCAT PGRP2 | 0.808 (0.667, 0.918) | 0.872 (0.798, 0.939) |
| HEMO IC1 KLKB1 | 0.842 (0.666, 0.927) | 0.892 (0.824, 0.942) |
| A2AP KLKB1 TRFE | 0.821 (0.666, 0.927) | 0.865 (0.800, 0.947) |
| A1AG1 A2MG HEMO | 0.824 (0.666, 0.940) | 0.887 (0.815, 0.943) |
| A1AG1 HEMO KLKB1 | 0.808 (0.659, 0.918) | 0.872 (0.805, 0.931) |
| A2MG HEMO MBL2 | 0.830 (0.654, 0.935) | 0.892 (0.829, 0.949) |
| HEMO IC1 LCAT | 0.825 (0.653, 0.932) | 0.879 (0.808, 0.938) |
| A2MG HEMO PGRP2 | 0.844 (0.652, 0.961) | 0.874 (0.796, 0.939) |
| F13B HEMO KLKB1 | 0.808 (0.643, 0.907) | 0.878 (0.810, 0.931) |
| KLKB1 PGRP2 TRFE | 0.824 (0.641, 0.915) | 0.876 (0.790, 0.932) |
| HEMO KLKB1 PGRP2 | 0.800 (0.637, 0.939) | 0.873 (0.801, 0.931) |
| A2MG HEMO KLKB1 | 0.812 (0.634, 0.933) | 0.879 (0.819, 0.945) |
| A2AP HEMO PGRP2 | 0.816 (0.633, 0.932) | 0.856 (0.786, 0.926) |
| A2MG KLKB1 TRFE | 0.811 (0.632, 0.932) | 0.878 (0.804, 0.937) |
| CPN2 HEMO KLKB1 | 0.804 (0.630, 0.922) | 0.871 (0.803, 0.936) |
| A1AG1 KLKB1 TRFE | 0.804 (0.630, 0.919) | 0.876 (0.806, 0.935) |

Figure 3:
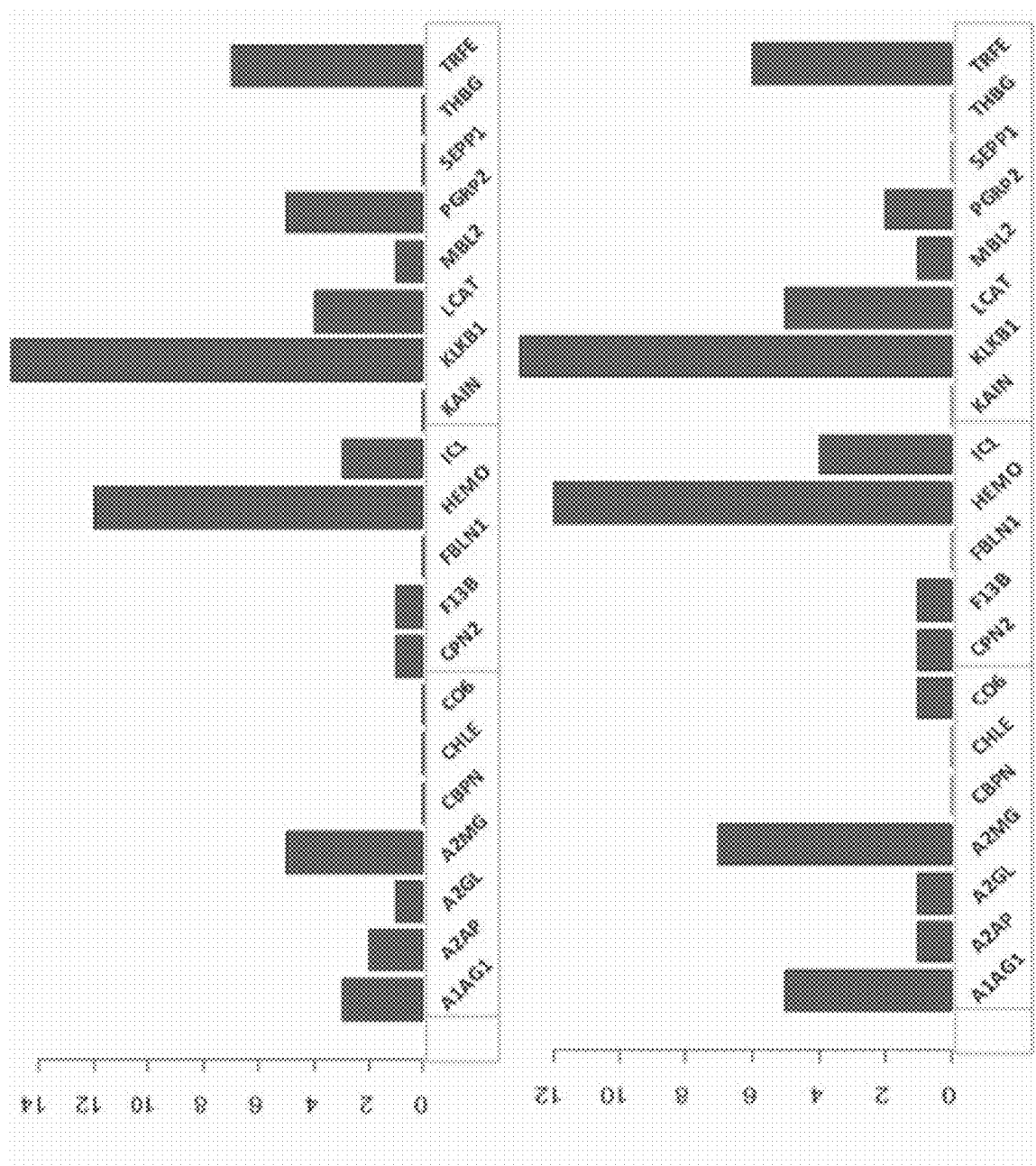
FIG. 3 shows the frequency of DDN-selected proteins in top 20 multivariate models based on AUC in Table 7 (top) or specificity at a fixed sensitivity of 80% in Table 8 (bottom).
Figure 4A:
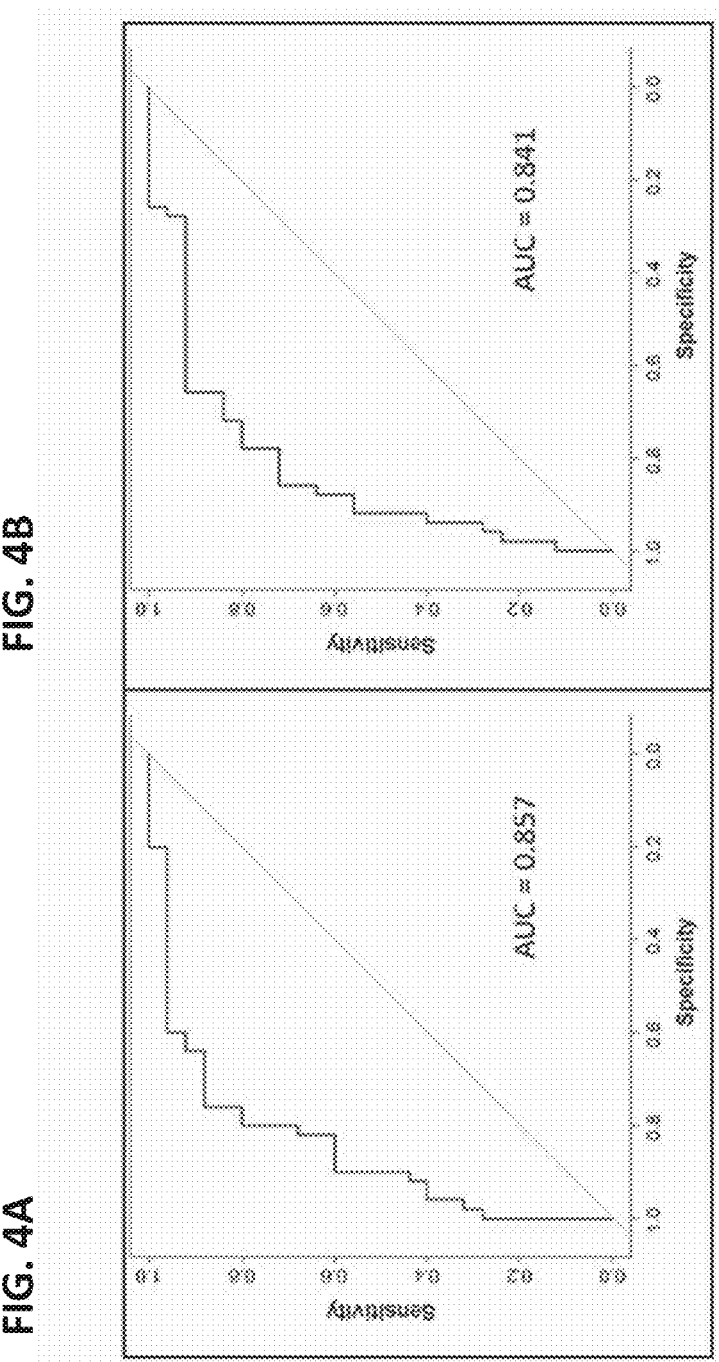
FIG. 4A and FIG. 4B show ROC curves of exemplary linear models combining three proteins. ROC analysis with bootstrap resampling provided an estimated range of performance in training data.
Figure 4B:
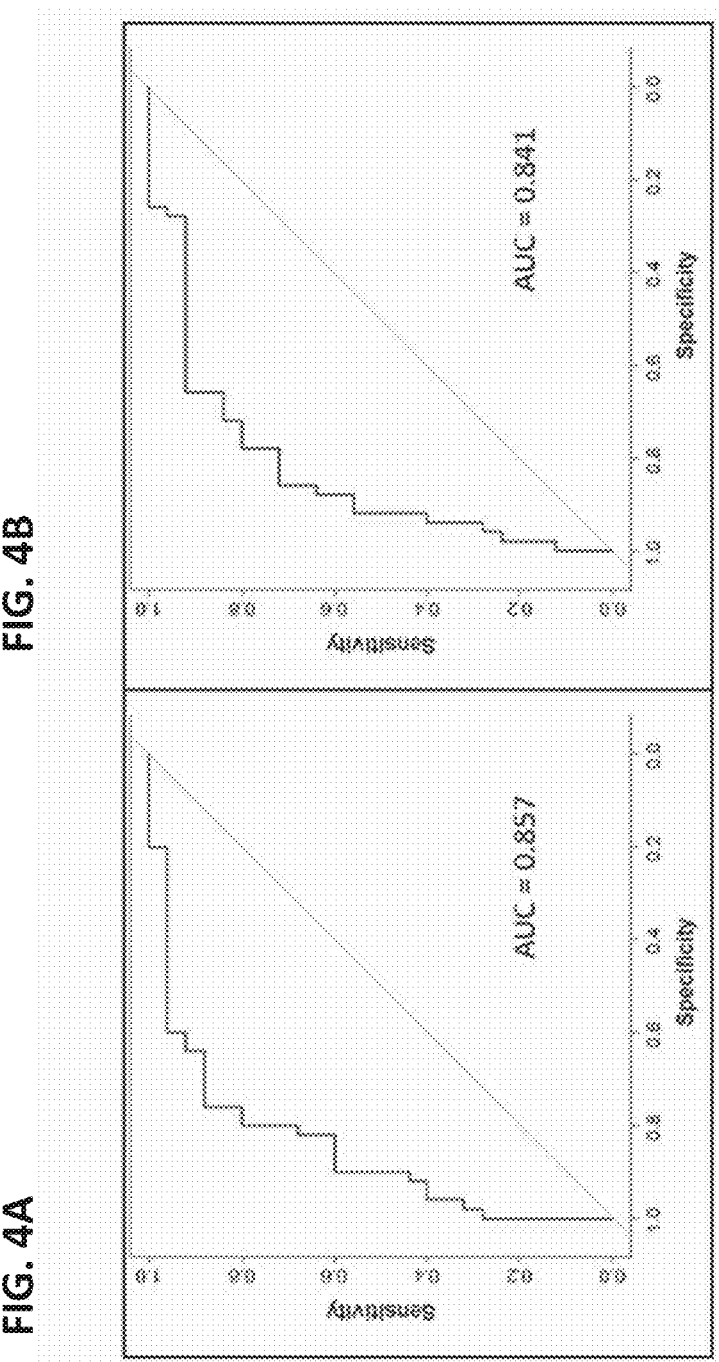

The frequency of individual proteins from the DDN analysis being included in the top 20 model panels was assessed. The protein biomarkers that appeared most frequently were HEMO, KLKB1, and TRFE (FIG. 3). The ROC curve and the AUC was determined by plotting sensitivity and specificity for exemplary linear models using two 3 protein panels (FIG. 4A and FIG. 4B): A2MG, HEMO and MBL2 (FIG. 4A) and KLKB1, IC1, and TRFE (FIG. 4B).

Protein biomarkers with an appreciable single analyte AUC were also selected for evaluation as multiplexing candidates: CBPN, CHLE, C9, F13B, HEMO, IC1, PROS and TRFE. The top 20 five-to-eight marker panels based on AUC and specificity at 75% sensitivity estimated using a linear model and bootstrap resampling.

TABLE 9

Top 20 Five-to-Eight Plex Multimarker Panels

| Panel | Specificity at 75% Sensitivity | | | Area Under the ROC Curve | | |
|---|---|---|---|---|---|---|
| | 5% CI | Median | 95% CI | 5% CI | Median | 95% CI |
| CBPN CHLE C9 F13B HEMO IC1 PROS | 0.7218 | 0.8857 | 0.9707 | 0.8245 | 0.8947 | 0.9539 |
| CBPN CHLE F13B HEMO IC1 PROS TRFE | 0.7352 | 0.8824 | 0.9730 | 0.8529 | 0.9061 | 0.9601 |
| CHLE F13B HEMO IC1 PROS TRFE | 0.7564 | 0.8784 | 0.9762 | 0.8430 | 0.9083 | 0.9638 |
| CBPN CHLE C9 F13B HEMO IC1 PROS TRFE | 0.7273 | 0.8750 | 0.9750 | 0.8363 | 0.9027 | 0.9561 |
| CBPN CHLE F13B IC1 PROS TRFE | 0.7218 | 0.8750 | 0.9715 | 0.8291 | 0.8963 | 0.9475 |
| CHLE C9 F13B HEMO IC1 PROS TRFE | 0.7419 | 0.8710 | 0.9737 | 0.8505 | 0.9032 | 0.9589 |
| CHLE F13B HEMO PROS TRFE | 0.7220 | 0.8703 | 0.9668 | 0.8337 | 0.8971 | 0.9484 |
| CBPN CHLE F13B HEMO IC1 PROS | 0.7368 | 0.8697 | 0.9723 | 0.8450 | 0.8960 | 0.9509 |
| CBPN CHLE C9 F13B HEMO PROS TRFE | 0.6869 | 0.8675 | 0.9737 | 0.8260 | 0.8986 | 0.9479 |
| CHLE C9 F13B HEMO PROS TRFE | 0.6998 | 0.8667 | 0.9697 | 0.8269 | 0.8972 | 0.9465 |
| CBPN CHLE C9 F13B PROS TRFE | 0.7185 | 0.8658 | 0.9723 | 0.8124 | 0.8834 | 0.9433 |
| CBPN CHLE HEMO IC1 PROS TRFE | 0.7493 | 0.8658 | 0.9707 | 0.8348 | 0.8946 | 0.9593 |
| CBPN CHLE C9 F13B IC1 PROS TRFE | 0.7241 | 0.8649 | 0.9706 | 0.8381 | 0.8971 | 0.9487 |
| CBPN CHLE F13B HEMO PROS | 0.6968 | 0.8649 | 0.9677 | 0.8068 | 0.8857 | 0.9422 |
| CHLE F13B IC1 PROS TRFE | 0.7199 | 0.8621 | 0.9737 | 0.8315 | 0.9014 | 0.9465 |
| CBPN CHLE F13B HEMO PROS TRFE | 0.7137 | 0.8616 | 0.9586 | 0.8299 | 0.8953 | 0.9523 |

TABLE 9-continued

Top 20 Five-to-Eight Plex Multimarker Panels

| Panel | Specificity at 75% Sensitivity | | | Area Under the ROC Curve | | |
|---|---|---|---|---|---|---|
| | 5% CI | Median | 95% CI | 5% CI | Median | 95% CI |
| CBPN CHLE HEMO IC1 PROS | 0.7218 | 0.8611 | 0.9730 | 0.8183 | 0.8852 | 0.9429 |
| CBPN F13B HEMO IC1 PROS TRFE | 0.6995 | 0.8611 | 0.9689 | 0.8102 | 0.8863 | 0.9508 |
| CHLE C9 F13B IC1 PROS TRFE | 0.7212 | 0.8611 | 0.9679 | 0.8212 | 0.8924 | 0.9525 |
| CHLE C9 F13B HEMO IC1 PROS | 0.7239 | 0.8571 | 0.9730 | 0.8368 | 0.8996 | 0.9555 |

The performance criteria include p-values, specificity at 75% sensitivity, and AUC from ROC analysis. For each criteria, there are three numbers corresponding to bootstrap estimated 95% confidence interval (5% CI, 95% CI) and median (50% CI).

Figure 4C:
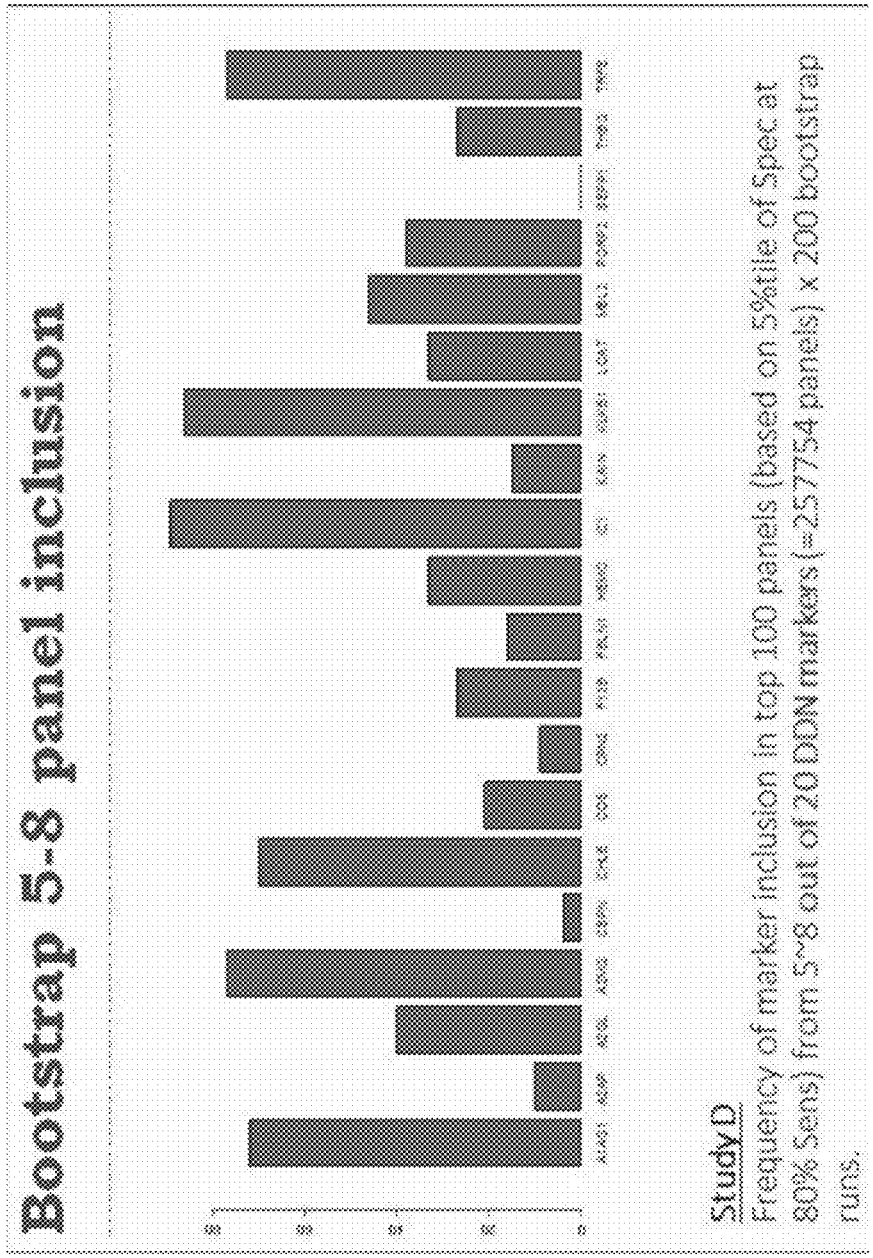
FIG. 4C shows the frequency of marker inclusion in the top 100 panels of five to eight microparticle-associated proteins.

FIG. 4C shows the frequency of marker inclusion in the top 1000 panels (based on 5 percentile of specificity, at 80% sensitivity from five-eight biomarker panels (multiplexes of five to eight proteins) of the 20DDN markers (=257754 panels)×200 bootstrap runs. The six markers that show the highest frequency are A1AG1, A2MG, CHLE, IC1, KLKB1, and TRFE.

Discussion

Numerous protein biomarkers associated with several clinically relevant biological processes that exhibit characteristic expression profiles by 10-12 weeks gestation among SPTB cases were identified. The protein biomarkers identified are primarily involved in inter-related biological networks linked to coagulation, fibrinolysis, immune modulation and the complement system (Table 10). These systems, in turn, are believed to have an interaction with adaptive immunity and the mediation of inflammatory processes necessary to sustain a successful pregnancy.

TABLE 10

Biological Pathways of CMP-Associated Protein Biomarkers

| Primary Functional Category | Biomarkers Identified | Additional Biomarkers |
|---|---|---|
| Coagulation/Wound Healing | F13A, F13B, FBLN1 | FA9, FA10, PROS, FIBA, FIBG, FINC, HABP2, PLF4 |
| Inflammation/Oxidative Stress | CBPN, CHLE, HEMO, TRFE, VTDB, PGRP2, CD5L, SEPP1, CPN2 | FETUA, FETUB, PON1, SAA4, GPX3 |
| Kinin-Kallikrein-Angiotensin System (coagulation + and complement interplay) | AACT, KLKB1, KNG1, KAIN | HEP2 |
| Complement/Adaptive Immunity | IC1, C9, CBPN, C6, C8A, HPT, MBL2, A2GL, A1AG1 | C7, ATRN, C1R, FCN3, HPTR, IGJ, MASP1, C8G, CLUS, A1AG2, A1BG |
| Fibrinolysis/Anti-coagulation/ITIH Related | ITIH1, ITIH2, ITIH4, AMBP, TRY3, A2AP, A2MG | A1AT, ZPI |
| Lipid Metabolism | APOM, APOL1, APOA1, LCAT | ZA2G, APOD, APOF |
| Thyroid Related | THBG, TTHY | THRB |

It is increasingly understood that immune dysregulation, aberrant coagulation and intrauterine inflammation are common to a large proportion of cases of SPTB (Romero et al., Science, 345:760-765, 2014). A high proportion of adverse pregnancy outcomes are believed to have their pathophysiologic origins in early pregnancy. Abnormalities of early placentation and trophoblast function have been observed not only in pregnancies complicated by hypertension, but also in approximately 30% of those experiencing SPTB (Kim et al., Am J Obstet Gynecol, 189:1063-1069, 2003). The state, condition, and function of cells at the maternal-fetal interface during this critical period have already predisposed the pregnancy to adverse outcomes. Others have observed that the concentration of placental-specific microparticles increases significantly with advancing gestation (Sarker et al., J Transl Med, 12:204, 2014). Early perturbations in microparticle-mediated signaling may gradually become magnified as the pregnancy progresses. Ultimately, the anomalies in the maternal fetal cross-talk may become sufficiently great to cause a network crash of the systems that were facilitating tolerance, resulting in a spontaneous preterm birth.

One of the traditional hindrances to a greater understanding of the underlying causes of SPTB is the difficulty of investigating the maternal-fetal interface itself and the unique nature of human placentation. The intrauterine space is both physically and ethically remote. As such, this is perhaps why, with the possible exception of the measurement of cervical length by ultrasound, little recent progress has been made in the development of useful biomarkers to stratify patients according to risk of SPTB (Conde-Agudelo et al., BJOG, 118:1042-1054, 2011). Differences in the protein content of microparticles represent an untapped source of information regarding biology of the maternal-fetal interface. As determined during development of the present disclosure, improved specificity (as indicated by increased AUC) can be obtained with the simultaneous consideration of multiple protein biomarkers associated with a CMP-enriched plasma fraction.

Example 2: Identification of SPTB Biomarkers in Samples Obtained Between 22-24 Weeks Gestation This example describes a study utilizing plasma samples obtained between 22-24 weeks gestation, from the same pregnant subjects of Example 1. The sample preparation, analysis and statistical methods were the same as that described for Example 1.

Figure 5:
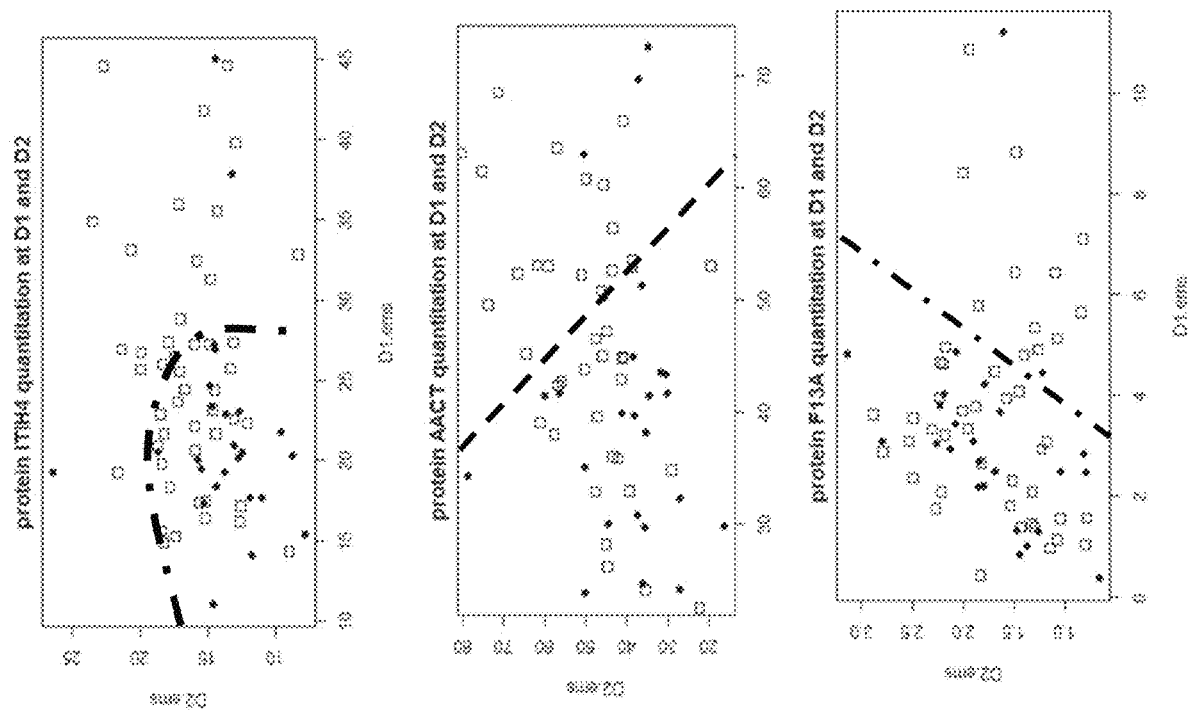
FIG. 5 shows temporal patterns in protein expression over two time points (D1=about 10-12 weeks gestation; D2=about 22-24 weeks gestation) carries differential information between SPTBs and controls.

As examples, measurements of three biomarkers (ITIH4, AACT, and F13A) analyzed in Example 1 (time point D1) were plotted against the proteins' corresponding measurements at the later time point of this example (time point D2). This is depicted in FIG. 5—there are different yet clear patterns between D1 and D2 measurements for individual biomarkers that can be used to improve separation between SPTBs and controls. Dash lines indicate possible classification boundaries between SPTB and controls using two time point measurements.

The following proteins displayed consistent performance as predictive for SPTB at week 10-12 (time point D1, Example 1) and week 22-24 (time point D2, this example): AACT, KLKB1, APOM, ITIH4, IC1, KNG1, C9, F13B, APOL1, LCAT, PGRP2, FBLN1, ITIH2, CDSL, CBPN, VTDB, AMBP, CBA, ITIH1, TTHY, and APOA1.

Example 3: Identification of a Subset of SPTB Biomarkers in Samples Obtained Between 10-12 Weeks Gestation This example describes a study utilizing plasma samples obtained between 10-12 weeks gestation. Using an independent cohort from that of Example 1, a set of markers was validated that, when obtained between 10-12 weeks, predict SPTB <35 weeks.

Methods:

Obstetrical outcomes in 75 singleton pregnancies with prospectively collected plasma samples obtained between 10-12 weeks were validated by physician reviewers for SPTB <35 weeks. These were matched to 150 uncomplicated singleton term deliveries. Controls were matched on gestational age at sampling (+/−2 weeks), maternal age (+/−2 years), race and parity. CMPs from these specimens were isolated and analyzed by multiple reaction monitoring mass spectrometry for known protein biomarkers selected from the previous study for their ability to predict the risk of delivery <35 weeks. The biological relevance of these analytes via a combined functional profiling/pathway analysis was also examined.

Data Analysis and Results:

Cases and controls did not differ by BMI (26 vs 25 kg/m$^2$; p=0.37) or in vitro fertilization (17% vs 10%; p=0.10) status respectively. Mean gestational age at delivery was 33 vs 39 weeks ($p<10^{-5}$). It was observed that the CMP markers identified in the previous study again demonstrated distinct Kaplan-Meier curves for SPTB.

Figure 6:
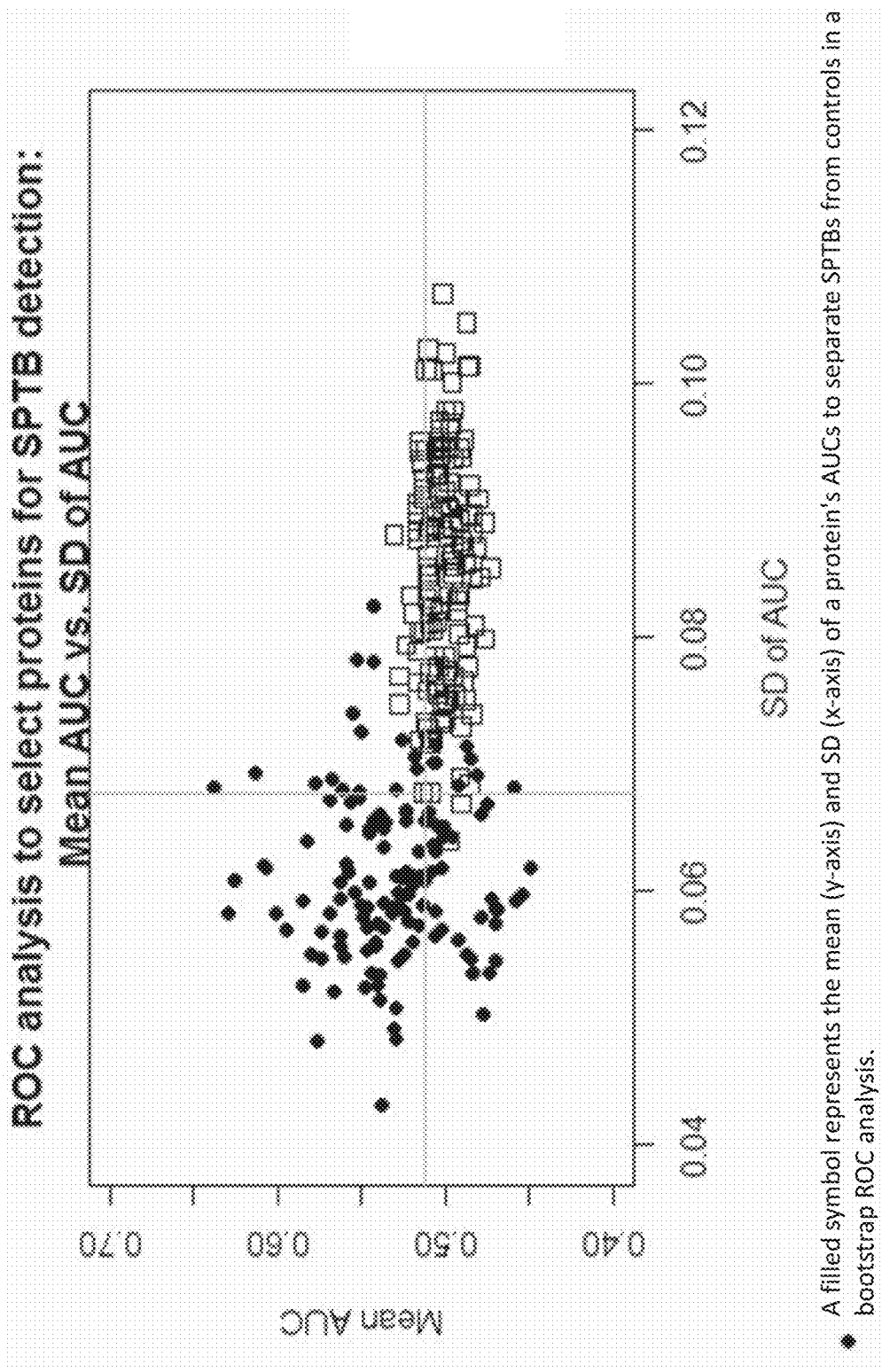
FIG. 6 shows a selection of proteins for SPTB detection.
Figure 7:
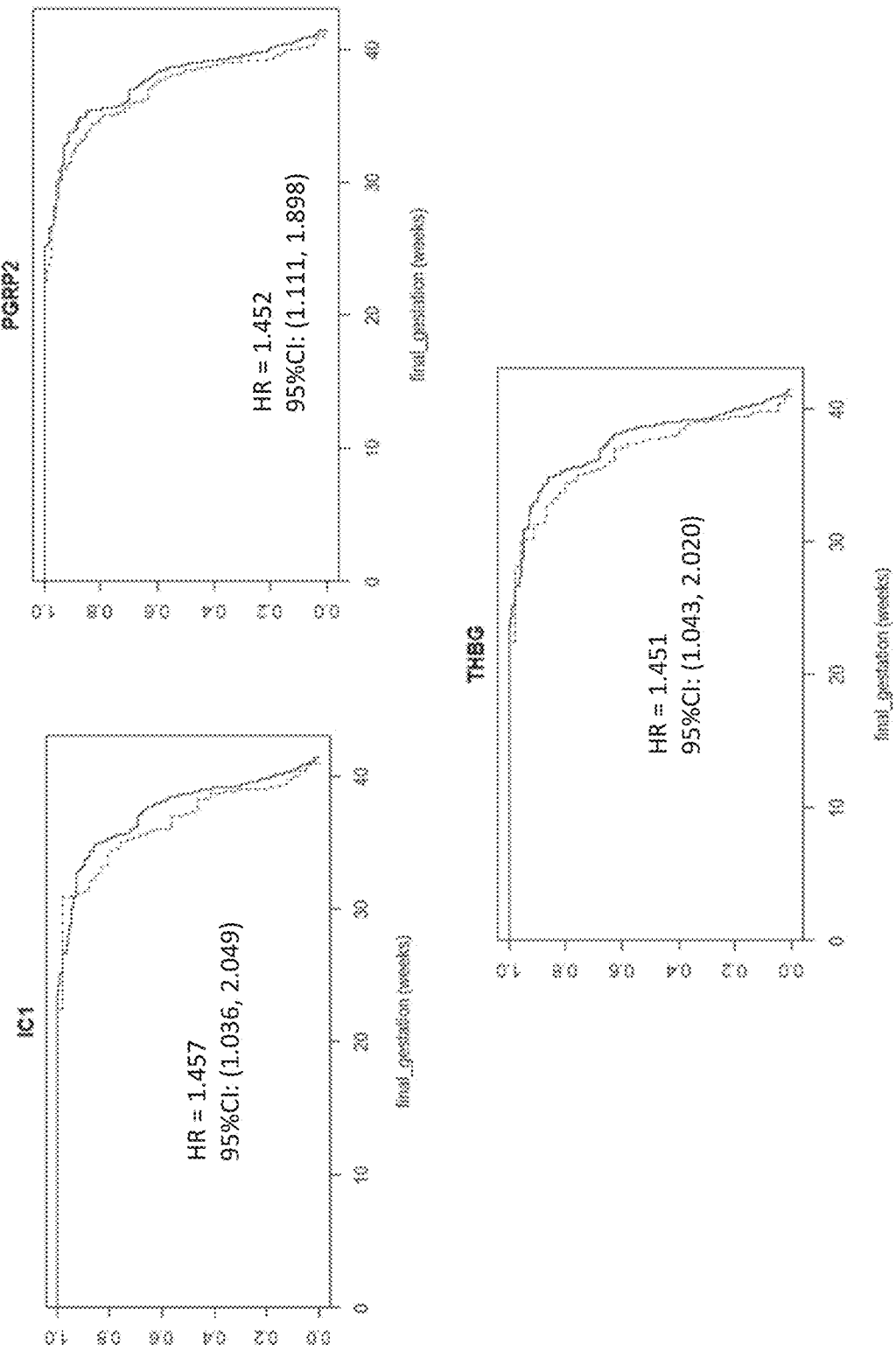
FIG. 7 shows proteins with statistically consistent performance.

As depicted in FIG. 6, SPTB patients and control samples were randomly sampled with replacement (bootstrap sampling) 50 times. Each time, a receiver-operating characteristic (ROC) curve was computed and the corresponding area-under-curve (AUC) was estimated. The mean (vertical axis) and standard deviation (horizontal axis) of AUCs estimated from the 50 bootstrap sampling runs were plotted for each candidate protein biomarkers (solid filled circles). The same procedure was repeated while the patient/control label of samples were randomly scrambled (label permutation) and the results were plotted as hollow squares, simulating how the results would appear if the protein biomarkers did not have any discriminatory power. The horizontal line indicates one standard deviation above the mean, both estimated from the label permutated results. The vertical line corresponds to one standard deviation above the mean, both estimated from the correctly labeled results. The solid circles in the upper-left quadrant are proteins that had relatively high and statistically stable discriminatory power. Using bootstrap sampling and label permutation analysis, a set of proteins listed in Table 2 above demonstrated statistically consistent differentiating power (as evidenced by ROC analysis) to separate SPTB from controls. A filled symbol represents the mean (y-axis) and SD (x-axis) of a protein's AUCs to separate SPTBs from controls in a bootstrap ROC analysis. A hollow square represents the mean and SD of AUCs of a protein from the same bootstrap ROC analysis yet with the sample's SPTB/control label randomly reassigned (permutated). As shown in FIG. 7, the proteins with statistically consistent performance are presented as filled circles in the upper-left quadrant of the plot.

It was noted that the following proteins displayed consistent performance between the sample set in Example 1 and the sample set in Example 3. These proteins are: KLKB1, APOM, ITIH4, IC1, KNG1, C9, APOL1, PGRP2, THBG, FBLN1, ITIH2, VTDB, C8A, APOA1, HPT, and TRY3.

Example 4: Sample Preparation Methods

The sample preparation methods were further investigated.

Figure 8:
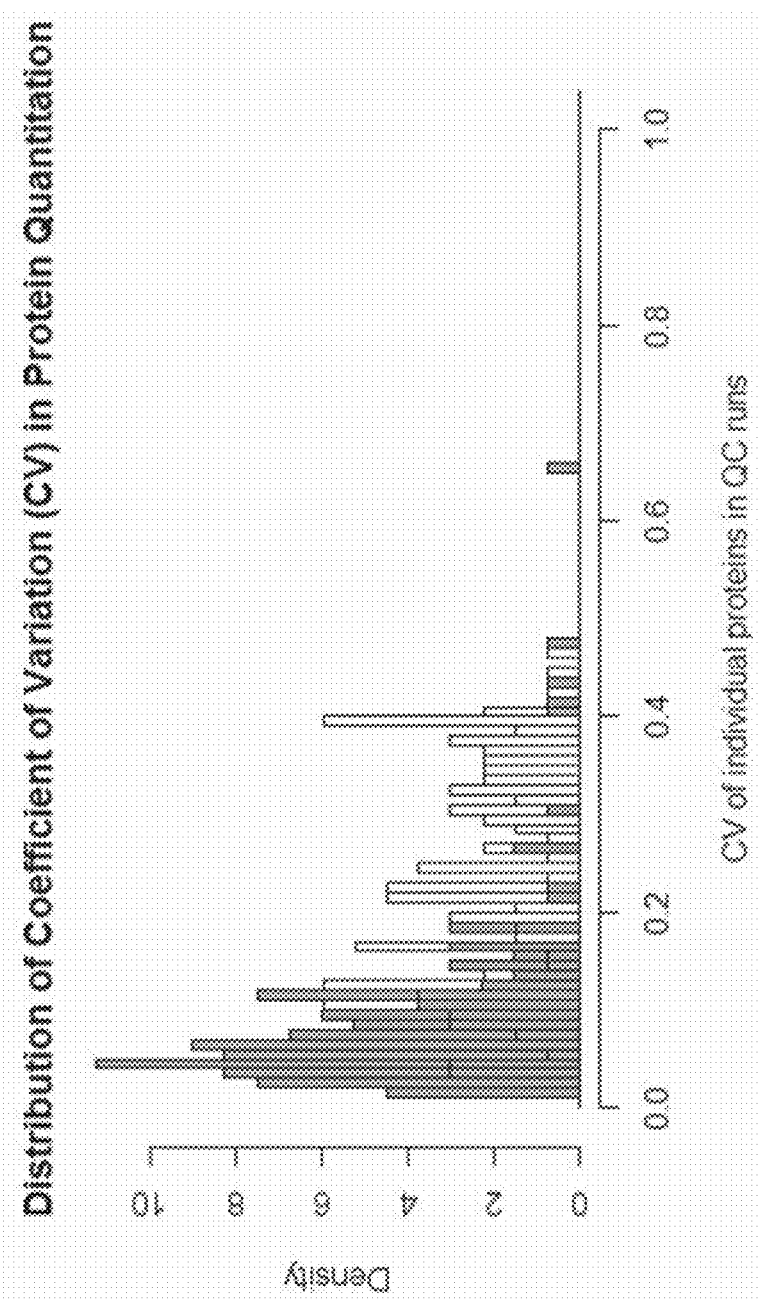
FIG. 8 shows that 2 pools in SEC data from samples in Example 2 demonstrate high analytical precision (small coefficient of variation).

FIG. 8 shows that 2 QC Pools in size exclusion chromatography (SEC) data from samples in Example 2 demonstrate high analytical precision (small coefficient of variation). Two pooled samples were used in sample set used for the data generation of Example 2 (22-24 weeks samples). The coefficient of variation (CV), a measure of analytical precision, was estimated for all proteins using the QC data as technical replicates. The distribution of CVs across all proteins were plotted as histograms. Pool A: shaded bars, Pool B: hollow bars. The analytical precision was proper for biomarker discovery research.

Figure 9:
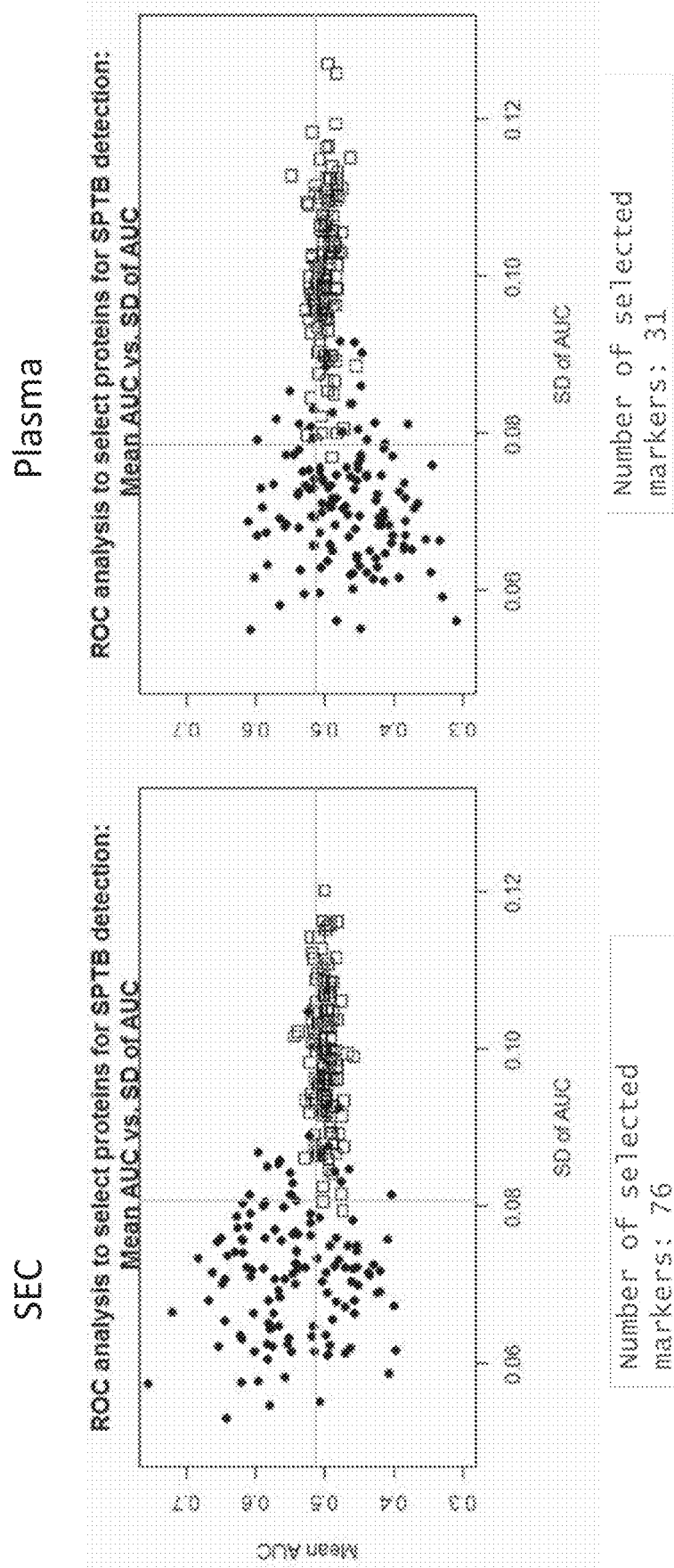
FIG. 9 shows the of NeXosome® sample prep step (SEC) on number of proteins informative in detecting SPTB from controls, from samples used in Example 2.
Figure 10:
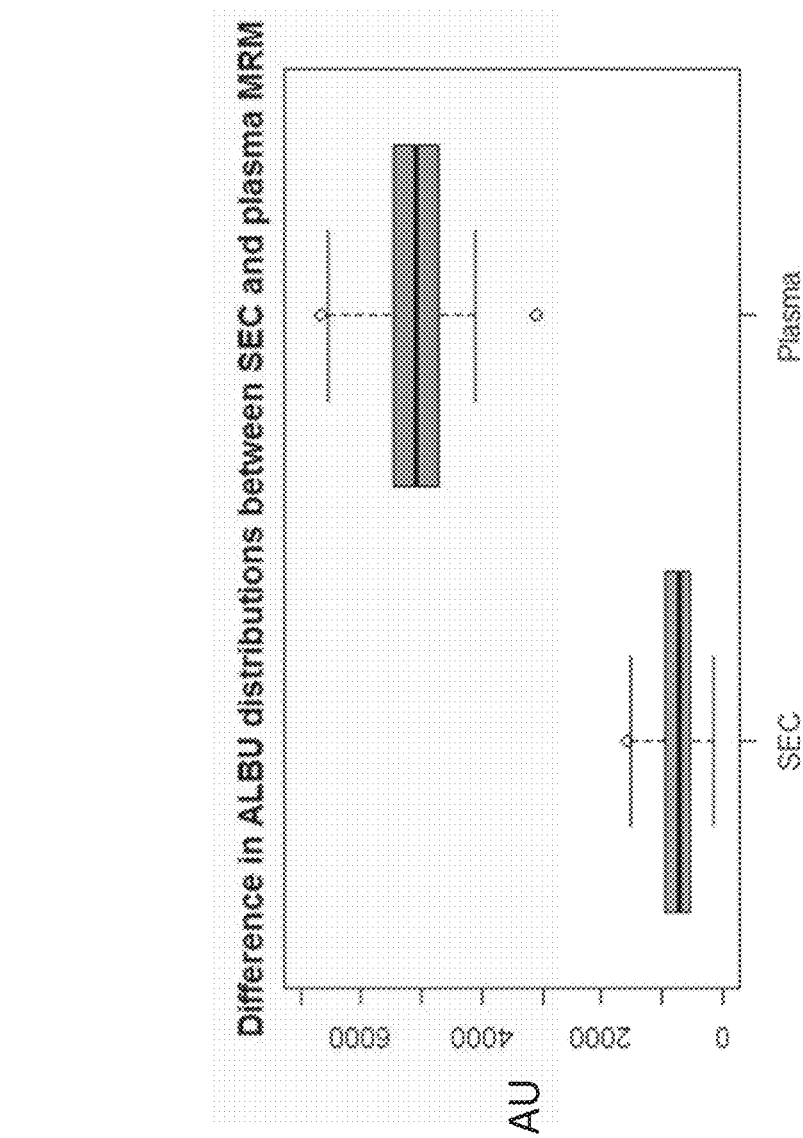
FIG. 10 shows the effect of SEC on concentration of abundant protein ALBU.

FIG. 9 shows the of NeXosome® sample prep step (SEC) on a number of proteins informative in detecting SPTB from controls, from the 22-24 week samples used in Example 2. The sample bootstrap biomarker selection procedure was applied to data generated from specimens with NeXosome sample preparation step and from plasma specimens directly, both from the same patients. Results show that a large number of informative proteins were identified from data of specimens with SEC. With NeXosome sample prep step (SEC), high value microparticles were enriched, and as a result, improved the identification of clinically informative and biologically relevant biomarkers for SPTB FIG. 10 shows the effect of SEC on concentration of abundant protein albumin (ALBU). Boxplots show distributions of albumin quantitation in samples with SEC prep and in plasma samples directly. The NeXosome sample prep step (SEC) reduced significantly albumin concentration in comparison to using plasma directly.

Figure 11:
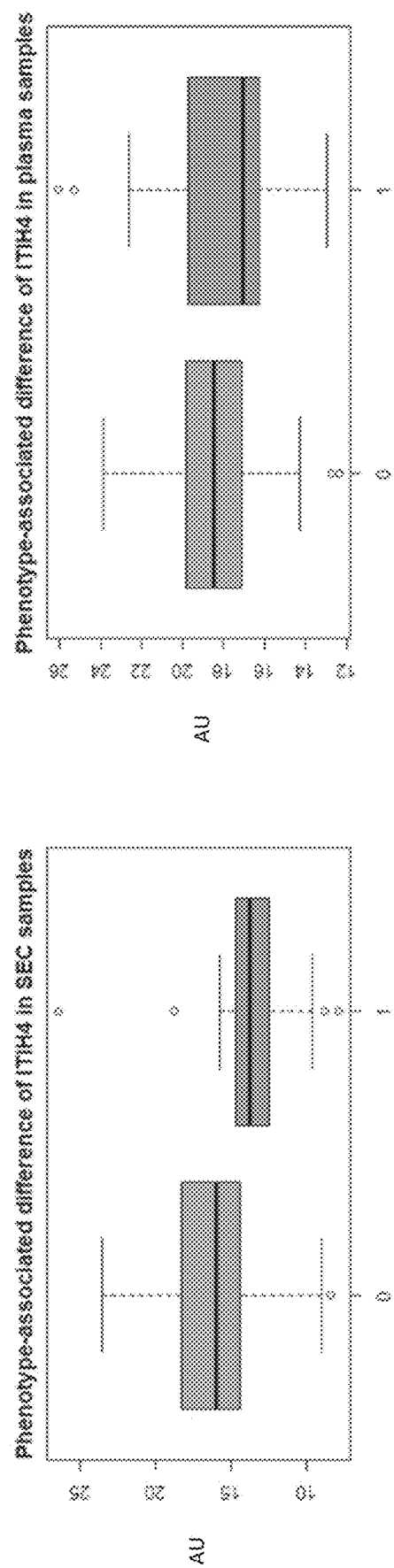
FIG. 11 shows that SEC improved separation between SPTB and controls in discrimination the biomarker ITIH4 in samples taken at 22-24 weeks gestation.

FIG. 11 shows that SEC improved separation between SPTB and controls in D2 ITIH4. Boxplots compare differences in distributions of biomarker ITIH4 between SPTBs and controls in samples with and without NeXosome sample prep step (SEC). SEC significantly improved separation between SPTB and controls for biomarker ITIH4 (p<0.0004 for data from SEC prep samples vs. p=0.3145 for data from plasma directly, Mann-Whitney-Wilcoxon Test).

While the described invention has been described with reference to the specific embodiments thereof it should be understood by those skilled in the art that various changes may be made and equivalents may be substituted without departing from the true spirit and scope of the invention. The various embodiments described above can be combined to provide further embodiments. In addition, many modifications may be made to adopt a particular situation, material, composition of matter, process, process step or steps, to the objective spirit and scope of the described invention. All such modifications are intended to be within the scope of the claims appended hereto.

The invention claimed is:

1. A method comprising administering to a human pregnant subject characterized as having a panel of microparticle-associated proteins indicative of an increased risk of spontaneous preterm birth, an effective amount of a treatment designed to reduce the risk of spontaneous preterm birth, wherein the panel comprises:
   (i) at least plasma protease C1 inhibitor (IC1), inter-alpha-trypsin inhibitor heavy chain H4 (ITIH4) and lecithin-cholesterol acyltransferase (LCAT);
   (ii) at least IC1, LCAT and serotransferrin (TRFE);
   (iii) at least four proteins selected from the group consisting of IC1, LCAT, fibulin 1 (FBLN1), coagulation factor XIII A chain (F13A) and inter-alpha-trypsin inhibitor heavy chain H2 (ITIH2); or
   (iv) at least IC1, LCAT, FBLN1, F13A and ITIH2,
   wherein the characterization of the panel is a based on a quantitative measure carried out on a microparticle-enriched fraction from a blood sample from the pregnant subject, and wherein the treatment is selected from the group consisting of cervical cerclage, a hormone and a corticosteroid.

2. The method of claim 1, wherein the treatment comprises vaginal progesterone or parenteral 17-alpha-hydroxyprogesterone caproate.

3. The method of claim 1, wherein the pregnant subject is a primigravida female.

4. The method of claim 1, wherein the sample is taken from the pregnant subject during the first or second trimester.

5. The method of claim 1, wherein the blood sample is a serum or plasma sample.

6. The method of claim 1, wherein the microparticle-enriched fraction is prepared using size-exclusion chromatography.

7. The method of claim 6, wherein the size-exclusion chromatography comprises elution with water.

8. The method of claim 6, wherein the size-exclusion chromatography is performed with an agarose solid phase and an aqueous liquid phase.

9. The method of claim 6, wherein the preparing step further comprises using ultrafiltration or reverse-phase chromatography.

10. The method of claim 6, wherein the preparing step further comprises denaturation using urea, reduction using dithiothreitol, alkylation using iodoacetamine, and digestion using trypsin prior to the size exclusion chromatography.

11. The method of claim 1, wherein determining a quantitative measure comprises mass spectrometry.

12. The method of claim 11, wherein determining a quantitative measure comprises liquid chromatography/mass spectrometry (LC/MS).

13. The method of claim 12, wherein the mass spectrometry comprises multiple reaction monitoring, the liquid chromatography is done using a solvent comprising acetonitrile, and/or the detecting step comprises assigning an indexed retention time to the proteins.

* * * * *

UNITED STATES PATENT AND TRADEMARK OFFICE
CERTIFICATE OF CORRECTION

PATENT NO. : 10,877,046 B2
APPLICATION NO. : 15/997540
DATED : December 29, 2020
INVENTOR(S) : Brohman et al.

Page 1 of 1

It is certified that error appears in the above-identified patent and that said Letters Patent is hereby corrected as shown below:

In the Claims

At Claim 1, Column 41, Line 16, replace:
"panel is a based on a"
With:
-- panel is based on a --

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*